(12) United States Patent
Honda et al.

(10) Patent No.: US 7,803,152 B2
(45) Date of Patent: Sep. 28, 2010

(54) METHOD AND APPARATUS FOR DETECTING A CONTROL SWITCH FOR MEDICAL EQUIPMENT

(75) Inventors: Yoshitaka Honda, Tokyo (JP); Kazue Tanaka, Sagamihara (JP); Hiroo Ono, Tokyo (JP)

(73) Assignee: Olympus Corporation, Tokyo (JP)

( * ) Notice: Subject to any disclaimer, the term of this patent is extended or adjusted under 35 U.S.C. 154(b) by 1509 days.

(21) Appl. No.: 10/957,238

(22) Filed: Oct. 1, 2004

(65) Prior Publication Data

US 2005/0075545 A1 Apr. 7, 2005

(30) Foreign Application Priority Data

Oct. 3, 2003 (JP) .............................. 2003-346232

(51) Int. Cl.
*A61B 18/04* (2006.01)
(52) U.S. Cl. ............................... 606/1; 606/32; 606/34; 200/86.5
(58) Field of Classification Search ..................... 606/1, 606/32–34; 200/61.39, 86.5; 434/11
See application file for complete search history.

(56) References Cited

U.S. PATENT DOCUMENTS

| 5,580,249 | A | * | 12/1996 | Jacobsen et al. | ............... 434/11 |
| 6,074,388 | A | * | 6/2000 | Tockweiler et al. | ........... 606/34 |
| 6,659,998 | B2 | * | 12/2003 | DeHoogh et al. | ............... 606/1 |
| 2002/0115917 | A1 | | 8/2002 | Honda et al. | |
| 2005/0004559 | A1 | * | 1/2005 | Quick et al. | ................... 606/1 |

FOREIGN PATENT DOCUMENTS

| JP | H11-318916 | 11/1999 |
| JP | 2002-238919 | 8/2002 |

* cited by examiner

*Primary Examiner*—Roy D Gibson
(74) *Attorney, Agent, or Firm*—Scully, Scott, Murphy & Presser, P.C.

(57) ABSTRACT

A control switch detecting apparatus aims at detecting a control switch operable by an operator for controlling a medical device. When a position signal for representing a position of at least one of the control switch and the operator is transmitted from at least one of the control switch and the operator, an obtaining unit obtains relative position information indicative of a relative positional relationship between the control switch and the operator based on the transmitted position signal.

16 Claims, 17 Drawing Sheets

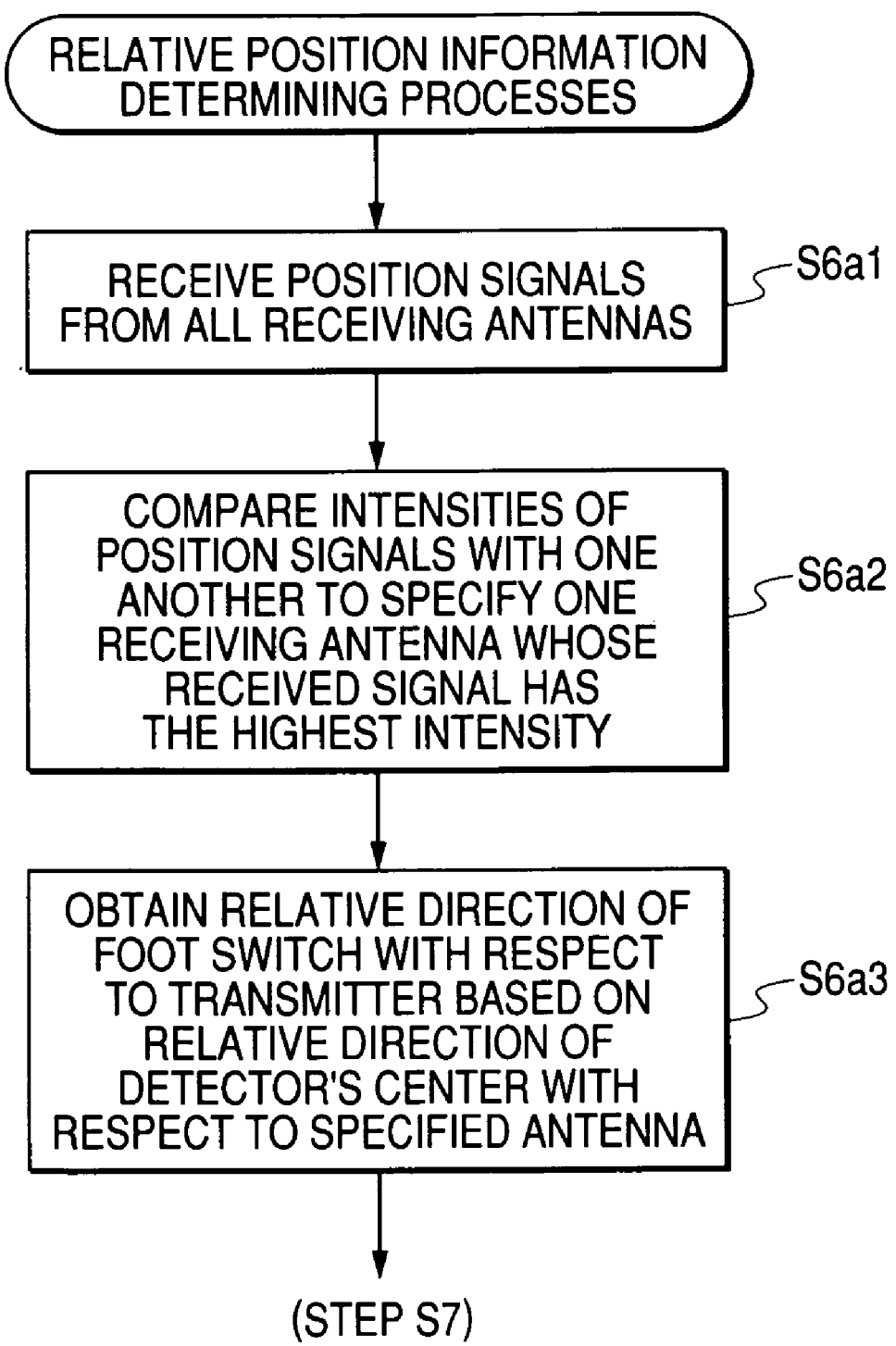

METHOD AND APPARATUS FOR DETECTING A CONTROL SWITCH FOR MEDICAL EQUIPMENT

BACKGROUND OF THE INVENTION

CROSS REFERENCE TO RELATED APPLICATION

This application is based upon the prior Japanese Patent Application 2003-346232 filed on Oct. 3, 2003 and claims the benefit of priority therefrom so that the descriptions of which are all incorporated herein by reference.

1. Field of the Invention

The present invention relates to a method and an apparatus for detecting a control switch that allows an operator to control the operation of at least one piece of medical equipment.

2. Description of the Related Art

Owing to the advances in medical technology in recent years, various pieces of medical equipment are being developed and put into practical use. Such medical equipment can be broadly divided into diagnostic monitoring equipment for monitoring and diagnosing tissues inside the body of a patient, and therapeutic treatment equipment for actually treating affected areas in the body parts of a patient.

The diagnostic monitoring equipment includes endoscopic systems, each having an endoscope for inspecting tissues of the body of a patient, and ultrasonic diagnostic systems, each of which is configured to generate ultrasonic images of tissues of the body of a patient based on ultrasonic echo signals therefrom for monitoring the tissues.

The therapeutic treatment equipment, which is designed to cut away and/or coagulate an affected area in the body of a patient with some treatment media, includes electric scalpel devices each using a high-frequency current, ultrasound-operating devices each using an oscillation of ultrasonic waves, and laser heat treatment instruments each using laser beam.

The diagnostic monitoring equipment and the therapeutic treatment equipment may be independently used, but recently, at least one piece of the diagnostic monitoring equipment and pieces of the therapeutic treatment equipment are often used in combination with each other.

In such a medical system designed to use at least one piece of the diagnostic monitoring equipment and pieces of the therapeutic treatment equipment together, an operator needs to specify one of the pieces of the therapeutic treatment equipment that matches an affected area in the body of a patient. After the specification of one of the pieces of the therapeutic treatment equipment, the operator needs to give operational instructions, for example, turn-on and turn-off instructions, to the specified piece of the therapeutic treatment equipment.

In particular, the operator operates a foot switch laid close to the operator's feet for specifying one of the pieces of the therapeutic treatment equipment and giving instructions to the specified piece. These controls of the therapeutic treatment equipment under the operations of the foot switch are disclosed, for example, in Japanese Unexamined Patent Publication H11-318916 and U.S. Pat. No. 6,679,875 corresponding to Japanese Unexamined Patent Publication No. 2002-238919.

SUMMARY OF THE INVENTION

The present invention is made in viewing the background set forth above, so that preferable embodiments of the present invention can improve conventional method and apparatus for detecting a control switch.

According to one aspect of the present invention, there is provided a control switch detecting apparatus for detecting a control switch operable by an operator for controlling a medical device. In the apparatus, a receiving unit is configured to receive a position signal for representing a position of at least one of the control switch and the operator. The position signal is transmitted from at least one of the control switch and the operator. In the apparatus, a determining unit is configured to determine relative position information indicative of a relative positional relationship between the control switch and the operator based on the received position signal.

According to another aspect of the present invention, there is provided a foot switch detecting apparatus for detecting a foot switch operable by an operator for controlling a medical device. In the apparatus, a transmitting unit is fitted to one of the foot switch and the operator and is configured to transmit a position signal for representing a position of one of the control switch and the operator. In the apparatus, a receiving unit is fitted to the other of the foot switch and the operator and is configured to receive the position signal transmitted from the transmitting unit. In the apparatus, a determining unit is configured to determine relative position information indicative of a relative positional relationship between the control switch and the operator based on the received position signal. In the apparatus, an output unit is configured to output the relative position information as information recognizable by the operator.

According to a further aspect of the present invention, there is provided a control switch communicable with a control unit for a control of a medical device and operable by an operator. In the control switch, a unit is configured to receive a position signal transmitted from the operator for representing a position of the operator and to transmit the received position signal to the control unit.

According to a still further aspect of the present invention, there is provided a controller communicable with a plurality of medical devices including a specific medical device and adapted to control them. In the controller, a first control switch is provided with a selection switch member operable by an operator and configured to select any one of the plurality of medical devices according to an operation of the selection switch member by the operator; and an output switch member operable by the operator and configured to output a control signal to the selected one of the medical devices according to an operation of the output switch member by the operator. In the controller, a second control switch has a switch member and operates to control the specific medical device according to an operation of the switch member. In the controller, an operation mechanism is engaged to the switch member of the second control switch. When the specific medical device is selected according to the operation of the selection switch member by the operator and the control signal is outputted to the specific medical device according to the operation of the output switch member by the operator, the operation mechanism operates the switch member of the second control switch according to the control signal.

According to a still further aspect of the present invention, there is provided a method of detecting a control switch operable by an operator for controlling a medical device. The method includes receiving a position signal for representing a position of at least one of the control switch and the operator. The position signal is transmitted from at least one of the control switch and the operator. The method also includes determining relative position information indicative of a relative positional relationship between the control switch and the operator based on the received position signal.

According to a still further aspect of the present invention, there is provided a method of operating, in response to an operation of a first control switch, a second control switch. The first control switch comprises a selection switch member operable by an operator and selectable any one of a plurality of medical devices including a specific medical device; and an output switch member operable by the operator for outputting a control signal. The second control switch has a switch member. The method includes, when the specific medical device is selected by the selection switch member according to an operation of the selection switch member by the operator and the control signal is outputted from the output switch member to the specific medical device according to an operation of the output switch member by the operator, receiving the outputted control signal. The method also includes automatically operating the switch member of the second control switch according to the received control signal.

BRIEF DESCRIPTION OF THE DRAWINGS

The invention will be more particularly described with reference to the accompanying drawings in which:

FIG. 5 is a flow chart schematically illustrating an example of operations of a control unit shown in FIG. 2;

DETAILED DESCRIPTION OF EMBODIMENTS OF THE INVENTION

Embodiments of the invention will be described hereinafter with reference to the accompanying drawings.

First embodiment

Figure 1:
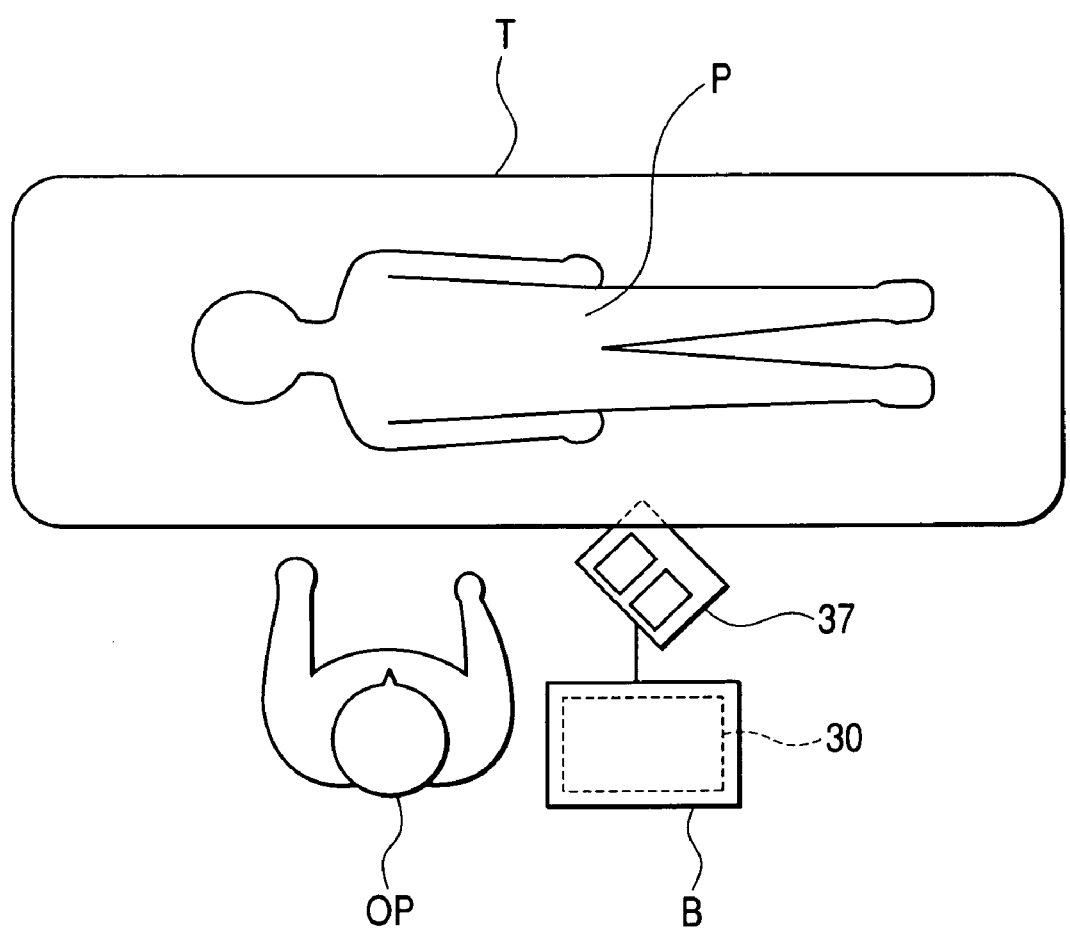
FIG. 1 is a plan view schematically illustrating a positional relationship between elements of a medical system according to a first embodiment of the present invention in an examination room in which the medical system is located.
Figure 2:
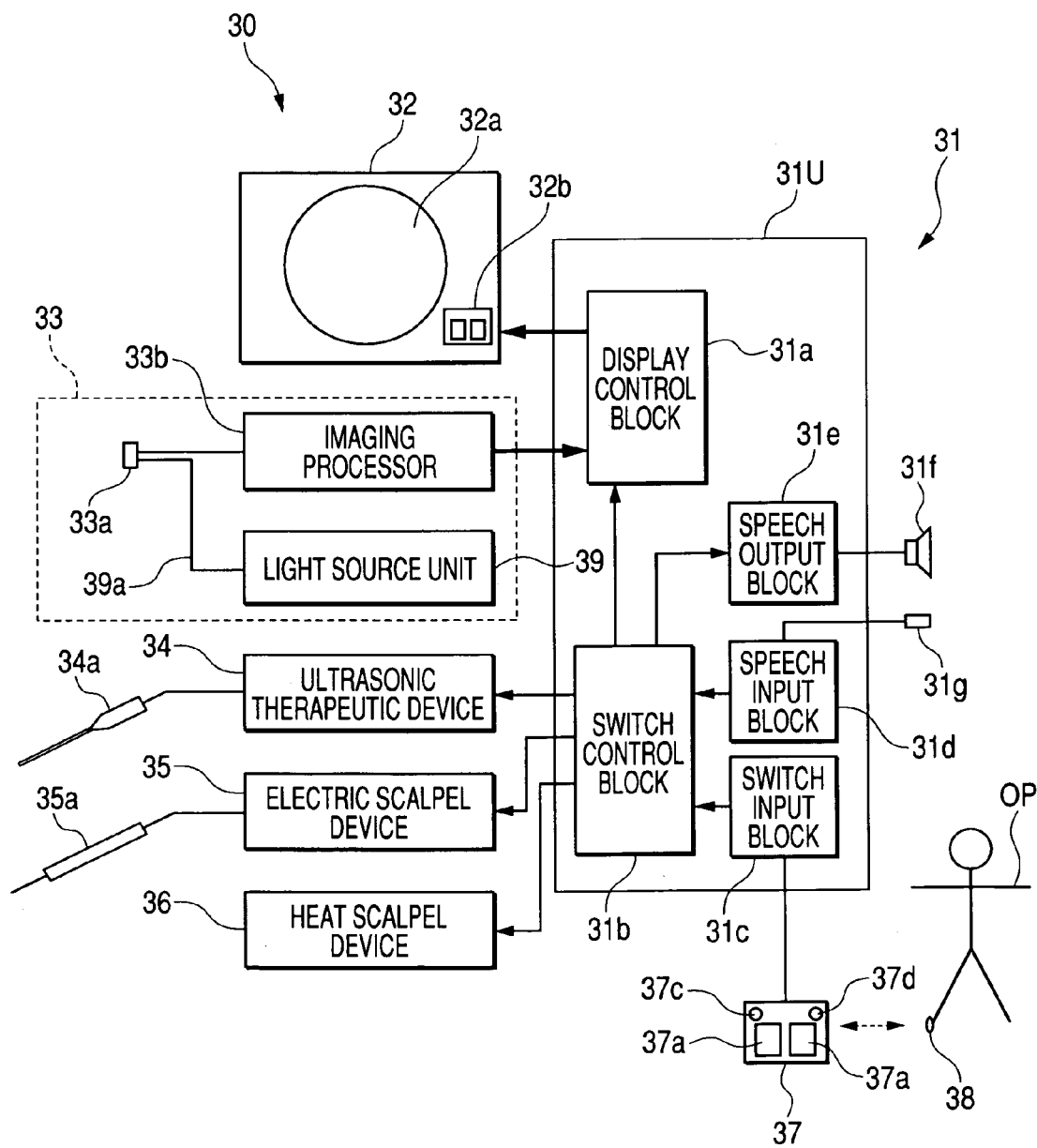
FIG. 2 is a block diagram illustrating a schematic structure of the medical system shown in FIG. 1.

FIG. 1 is a plan view schematically illustrating a positional relationship between elements of a medical system including a control switch detecting apparatus according to a first embodiment of the present invention in an examination room in which the medical system is located. FIG. 2 is a block diagram illustrating a schematic structure of the medical system shown in FIG. 1.

As shown in FIGS. 1 and 2, the medical system 30 related to the first embodiment is equipped with an electronic endoscopic device 33 and pieces of therapeutic treatment equipment including an ultrasonic therapeutic device 34, an electric scalpel device 35, and a heat scalpel device 36. That is, the medical system 30 is designed to an endoscopic system.

For example, the medical system 30 is so configured that all of the devices 33 to 36 are installed in a movable gantry B. In the examination room, an operating table T is previously placed, and a patient P as a target for inspection and treatment lies on the operating table T. The medical system 30 (the movable gantry B) is arranged close to the operating table T.

The medical system 30 is equipped with a foot switch 37 that allows an operator OP to specify one of the therapeutic treatment devices 34-36 and to instruct the identified device to control it, such as to turn it on or off. The foot switch 37 is laid at, for example, a desirable position for the operator OP in the examining room, such as close to the operator's feet, the operating table T, and the gantry B.

In particular, the operator OP operates the foot switch 37 with the operator's foot at desired times to select one of the therapeutic treatment devices 34-36, thereby turning the selected device on and/or off.

The medical system 30 is provided with, as shown in FIG. 2, a medical system controller 31 having a control unit 31U communicable with the electronic endoscope device 33, the ultrasonic therapeutic device 34, the electric scalpel device 35, the heat scalpel device 36, and the foot switch 37, respectively, by wire cables or radio. The medical system 30 is provided with a display 32 communicable with the control unit 31U.

The medical system 30 is provided with a position signal transmitter 38 fitted to a predetermined portion of the operator OP, for example, the ankle with a fitting member, such as a fitting band. The position signal transmitter 38 is operative to continuously or periodically transmit, for example, non-directional signals, such as radio signals or infrared signals, at predetermined frequencies around the transmitter 38. The signals transmitted from the position signal transmitter 38 are referred to as position signals.

The electronic endoscope device 33, as shown in FIG. 2, is equipped with an endoscope 33a. The endoscope 33a has a fiberscope, an image pickup device, such as a CCD (Charge Coupled Device) image sensor, mounted inside the fiberscope, and an optical system mounted inside the fiberscope for focusing light irradiated from one tip end of the fiberscope on a surgical field of the patient P.

The electronic endoscope device 33 is provided with a light source unit 39 optically coupled to the endoscope 33a through a light guide 39a. The light source unit 39 has a lamp and a lighting control circuit for controlling the lighting of the lamp. The lighting control circuit turns on the lamp so that the lamp irradiates light. The light is guided through the light guide 39a into the fiberscope of the endoscope 33a.

The electronic endoscope device 33 has an imaging processor 33b electrically connected to the image pickup device and operative to execute predetermined image processes with respect to an image signal picked up by the image pickup device.

That is, in the electronic endoscope device 33, the light irradiated from the fiberscope of the endoscope 33a is focused by the optical system on the surgical field of the patient P. A light reflected from an area of the patient P including the surgical field is inputted to a light-sensitive surface of the image pickup device so as to be picked up thereby as the image signal. The image signal is inputted to the imaging processor to be subjected to the predetermined image processes thereby so that an endoscope image signal indicative of an endoscope image of the surgical field is generated. The endoscope image signal generated by the imaging processor 33b is transmitted to the medical system controller 31.

On the other hand, the ultrasonic therapeutic device 34 has an ultrasonic therapeutic instrument 34a. The ultrasonic therapeutic device 34 is operative to supply energy to the ultrasonic therapeutic instrument 34a to cause it to operate. The operated ultrasonic therapeutic instrument 34a generates ultrasonic waves and the generated ultrasonic waves are applied to at least a part of the surgical field, allowing the part of the surgical field to be cut away and/or to coagulate.

The electric scalpel device 35 has an electric scalpel 35a. The electric scalpel device 35 is configured to apply a high-frequency current on at least a part of the surgical field through the electric scalpel 35a, thereby cutting off the part of the surgical field and/or coagulating it.

The heat scalpel device 36 has a heat scalpel (not shown). The heat scalpel device 36 is configured to apply heat energy on at least a part of the surgical field through the heat scalpel, thereby cutting off the part of the surgical field and/or coagulating it.

In addition, the medical system controller 31 is provided with a microphone 31g electrically connected to the control unit 31U and operative to input speech signals to the control unit 31U. The medical system controller 31 is provided with a speaker 31f electrically connected to the control unit 31U and operative to output speech signals transmitted from the control unit 31U.

The control unit 31U, as shown in FIG. 2, has a plurality of functional blocks including a display control block 31a, a switch control block 31b, a switch input block 31c, a speech input block 31d, and a speech output block 31e. The functional blocks 31a to 31e are operatively connected with each other.

The control unit 31U is composed of a computer circuit including, for example, at least one microcomputer. At least one microcomputer is integrated with a memory in which program codes are installed through various types of storage mediums or a communication line linked to the Internet. The various types of storage mediums include CD-ROM (Compact Disk—Read Only Memory), DVD-ROM (Digital Versatile Disk—ROM), and the like. The control unit 31U is configured to implement the respective functions 31a to 31e as processes in accordance with the program codes.

The display control block 31a has a first function of receiving the endoscope image signal supplied from the image processor 33. The display control block 31a has a second function of receiving selection information of the therapeutic treatment equipment that is obtained by the switch control block 31b to generate a selection image signal indicative of a selection image 32b. The selection image 32b allows the operator OP to recognize one of the therapeutic treatment devices 34-36 that is selected by the operator OP and the operation mode of the selected one of the therapeutic treatment devices 34-36.

Moreover, the display control block 31a has a third function of superimposing the generated selection image signal on the received endoscope image signal to supply the superimposition signal to the display 32, causing the display 32 to display the superimposition signal on its screen.

The switch control block 31b has a first function of receiving the selection information transmitted from the foot switch 37 or the microphone 31g. The selection information preferably includes information that permits the switch control block 31b to recognize an identifier of one device of the therapeutic treatment devices and its operating mode. As the identifier, the designation of the selected device and/or the identification codes thereof can be used.

The switch control block 31b has a second function of specifying one device of the therapeutic treatment devices and the operation mode that correspond to the received selection information.

The switch control block 31b has a third function of receiving operational instruction information, such as on/off instruction information, to send the received operational instruction information to the specified device.

The switch control block 31b has a fourth function of outputting the received selection information to either the display control block 31a or the speech output block 31e.

The switch input block 31c has a function of receiving the selection information and the operational instruction information sent from the foot switch 37 to supply the received selection information and operational instruction information to the switch control block 31b.

At least one of the selection information, the operational instruction information, and relative position information, which is generated by the operator OP as a speech, is converted into a speech signal by the microphone 31g to be amplified thereby and the amplified speech signal is inputted to the speech input block 31d.

When the amplified speech signal is inputted to the speech input block 31d, the speech input block 31d has a first function of receiving the inputted speech signal. The speech input block 31d has a second function of specifying at least one of the selection information, the operational instruction information, and relative position information based on the received speech signal to supply it to the switch control block 31b.

The speech output block 31e has a function of converting at least one of the selection information and the relative position information that is outputted from the switch control block 31b into a speech signal recognizable by the operator OP to put the speech signal on the speaker 31f.

The display 32 has a first function of receiving the superimposition signal on which the endoscope image signal and the selection image signal are superimposed transmitted from the display control block 31a. The display 32 has a second function of superimposing an endoscope image 32a of the surgical field and the selection image 32b to display the superimposed image on its screen based on the received superimposition signal. The display 32 executes the second function cooperatively with the control processes of the display control block 31a based on its second function.

Figure 3B:
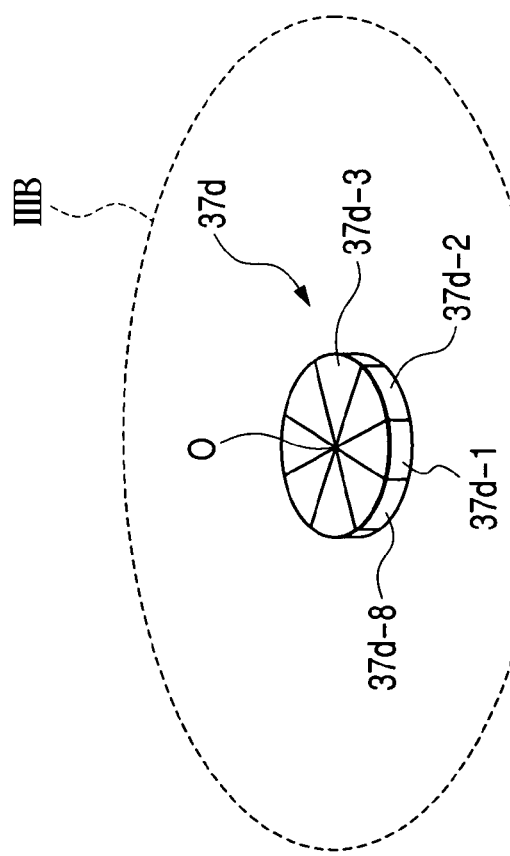
FIG. 3B is an enlarged perspective view schematically illustrating a relative position detector attached to the foot switch shown in FIG. 3A.
Figure 3A:
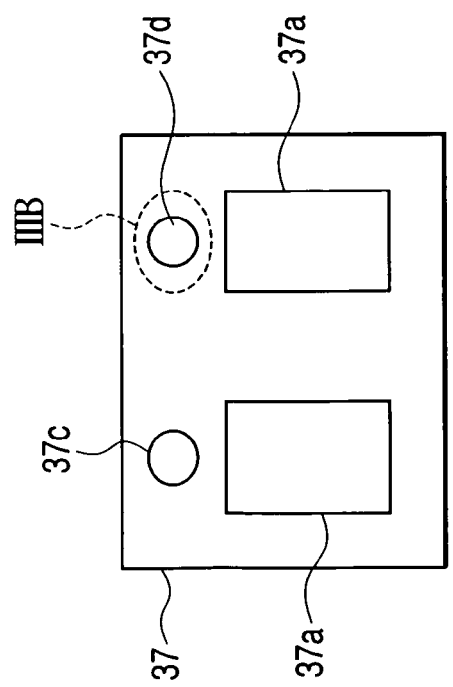
FIG. 3A is a plan view schematically illustrating a foot switch shown in FIG. 2.

The foot switch 37, as shown in FIG. 2 and FIG. 3A, has a foot-operated selection switch 37c for selecting any one of the therapeutic treatment devices 34-36. That is, the selection switch 37c is configured to output the selection information for selecting one of the therapeutic treatment devices 34-36 and its operation mode to the switch control block 31b through the switch input block 31c.

The foot switch 37 has a pedal output switch, in other words, foot-operated output switch 37a for outputting the operational instruction information indicative of the turning-on or turning-off of the selected device to the switch control block 31b through the switch input block 31c.

The output switch 37a is configured to a twin-type output switch (see FIGS. 2, 3A and so on).

The foot switch 37 has a relative position detector 37d configured to receive the position signals outputted from the position signal transmitter 38, representing a position of the position signal transmitter 38, in other words, the operator OP.

The selection switch 37c attached to the foot switch 37 is, for example, a momentary push button switch. That is, the selection switch 37c is configured to output operation information as the selection information to the switch control block 31b through the switch input block 31c each time the operator OP pushes the selection switch 37c with the operator's foot.

The switch control block 31b is configured to select one of the therapeutic treatment devices 34-36 and its operation mode in all of the previously determined operation modes of each of the therapeutic treatment devices 34-36 each time the selection information is transmitted through the switch input block 31c to the switch control block 31b.

For example, each time the selection information is transmitted through the switch input block 31c to the switch control block 31b the switch control block 31b sequentially selects one of the combinations of the therapeutic treatment devices 34-36 and their operation modes. The combinations indicate:

(1) operation of the ultrasonic therapeutic device 34 at 100% output (2) operation of the ultrasonic therapeutic device 34 at 70% output (3) operation of the electric scalpel device 35 at a predetermined output (4) operation of the heat scalpel device 36 at a predetermined output That is, the switch control block 31b selects both one therapeutic treatment device and its operation mode simultaneously.

The selection information indicative of the identifier of one of the therapeutic treatment devices and its operating mode which are switchably selected every operation of the operator's selection switch 37c is supplied from the switch control block 31b to the display control block 31a. The display control block 31a generates the selection image signal according to the selection information supplied thereto.

The display control block 31a displays on the center of the screen of the display 32 with the selection image 32b superimposed on, for example, the right corner of the screen as the operator faces.

The selection image 32b permits the operator OP and/or an assistant to easily recognize the currently selected therapeutic treatment device and its operating mode. Specifically, the operator OP operates to continuously turn the selection switch 37c of the foot switch 37 while visually identifying the selection image 32b, and when a therapeutic treatment device that the operator OP wants to use is displayed on the screen of the display 32, the operator OP stops the on-operations. This makes easy the operator's selection of a desirable therapeutic treatment device and its operating mode.

The output switch 37a attached to the foot switch 37 is a momentary pedal switch. That is, the output switch 37a has outputted the turn-on instruction information through the switch input block 31c to the switch control block 31b while the operator OP pushes the output switch 37a with the operator's foot.

The switch control block 31b transmits, to the therapeutic treatment device selected on the selection information, the operational instruction information for causing the selected device to operate in the selected operating mode.

The therapeutic treatment device to which the operational instruction information is transmitted operates in the selected operating mode, which allows the operator OP to use the operator's selected therapeutic treatment device operating in the operator's selected operating mode to treat the surgical field of the patient P.

In place of operating the selection switch 37c of the foot switch 37, speech input through the microphone 31g allows the therapeutic treatment device and its operation mode to be selected.

Specifically, when the operator OP produces a speech indicative of the selection information including the identifier of one of the therapeutic treatment devices 34-36, which the operator OP wants to use, and the operation mode thereof, the produced speech corresponding to the selection information is converted into electric signals by the microphone 31g and amplified thereby. The amplified electric signals are supplied to the speech input block 31d as speech signals.

The speech input block 31g receives the supplied speech signals and analyzes the received speech signals to detect the selection information, that is, the identifier of the selected device and its operating mode. The speech input block 31g supplies the detected selection information to the switch control block 31b.

The switch control block 31b performs the selection processes of one of the therapeutic treatment devices and its operating mode based on the supplied selection information in the same manner as the selection information supplied from the foot switch 37. Incidentally, the operational instruction information, such as turning-on or turning-off information, of the therapeutic treatment device selected according to the speech inputted from the microphone 31g is inputted from the operator OP through the output switch 37a of the foot switch 37 to the switch control block 31b. The switch control block 31b transmits the operational instruction information to the selected device so that the selected device is controlled based on the operational instruction information.

Next, the relative position detector 37d attached to the foot switch 37 will be explained.

Figure 3C:
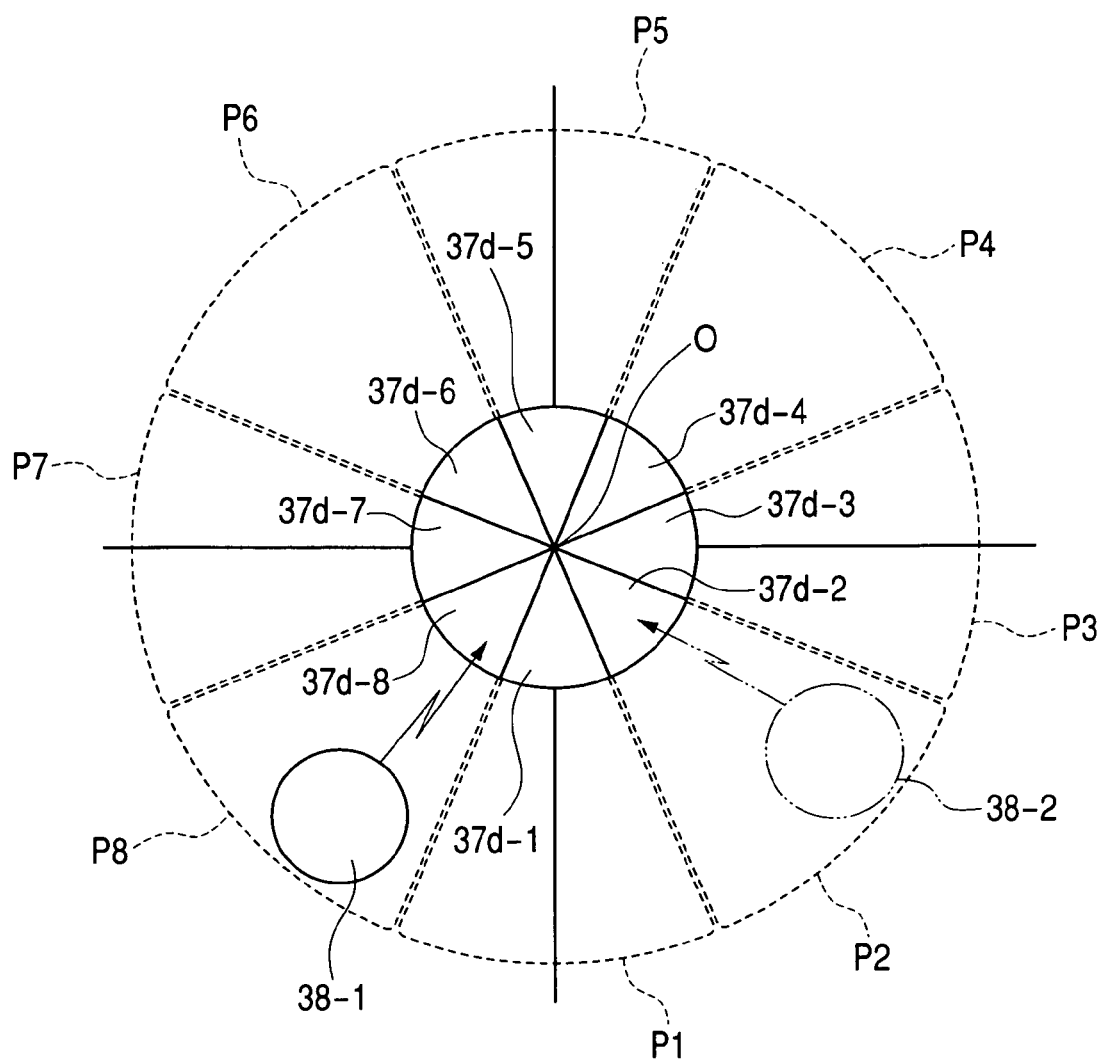
FIG. 3C is an enlarged view schematically illustrating directional receiving patterns of the relative position detector along a horizontal surface according to the first embodiment of the present invention.

As shown in FIGS. 3A to 3C, the relative position detector 37d attached to the foot switch 37 is provided with a metal antenna body having a substantially circular plate as a whole. The antenna body is preferably radially divided into a number of, such as 8, equal pieces from the center O thereof. The pieces of the metal antenna body serve as receiving antennas 37d-1, 37d-2, . . . , 37d-8, which have individual receiving directivities with respect to the position signals transmitted from the position signal transmitter 38, respectively.

As specifically illustrated in FIGS. 3B and 3C, each of the receiving antennas 37d-1 to 37d-8 has a substantially fan-like shape in its cross section parallel to the radial direction. Each of the receiving antennas 37d-1 to 37d-8 has a receiving unit operative to receive the position signals each with the predetermined frequency transmitted from the position signal transmitter 38. Each of the receiving antennas 37d-1 to 37d-8 also has an amplifier operative to amplify the position signals received by the receiving unit, and an output unit operative to output the amplified position signals.

Each of the receiving antennas 37d-1 to 37d-8 has a circular arc end surface, and each of directional receiving patterns P-1 to P-8 has a high sensitivity to some of the position signals transmitted from an area radially extending from the circular arc end surface. Viewing from above, FIG. 3C shows the directional receiving patterns P-1 to P-8 around the relative position detector 37d along a horizontal surface, such as a floor surface of the examining room on which the operator OP is movable. Each of the directional receiving patterns P-1 to P-8 along a vertical direction orthogonal to the horizontal direction has a high sensitivity to some of the position signals positioned in a predetermined range centered at each of the circular arc end surface and expanding along the vertical direction.

Each of the directional receiving patterns P-1 to P-8 of each of the receiving antennas 37d-1 to 37d-8 allows the relative position detector 37d to detect the position signals around the relative position detector 37d with great sensitivity.

The receiving antennas 37d-1 to 37d-8 are individually communicable with the control unit 31U of the medical system controller 31 by wire cables or radio. The receiving antennas 37d-1 to 37d-8 are respectively driven in response to driving signals transmitted from the switch input block 31c to operate to detect the position signals. The receiving antennas 37d-1 to 37d-8 further operate to individually transmit the detected signals through the switch input block 31c to the switch control block 31b. The receiving antennas 37d-1 to 37d-8 may be independently driven at all times or in a cycle, to detect the position signals. In this modification, the receiving antennas 37d-1 to 37d-8 operate to individually independently transmit the detected position signals through the switch input block 31c to the switch control block 31b.

The switch control block 31b has a fifth function of determining information indicative of a relative positional relationship between the foot switch 37 and the operator OP, in other words, between the position signal transmitter 38 and the relative position detector 37d, according to the position signals detected by the receiving antennas 377d-1 to 37d-8.

The information determined based on the fifth function of the switch control block 31b is referred to as "relative position information" hereinafter.

The relative position information between the position signal transmitter 38 and the relative position detector 37d preferably includes a direction of the position signal transmitter 38 with respect to the relative position detector 37d and/or a distance between the position signal transmitter 38 and the relative position detector 37d.

For example, when the position signals are detected by the receiving antennas 37d-1 to 37d-8, respectively, and are supplied through the switch input block 31c to the switch control block 31b, the switch control block 31b compares the intensities of the position signals of the respective receiving antennas 37d-1 and 37d-8 with one another. As a result of the comparison, the switch control block 31b specifies one of the receiving antennas 37d-1 to 37d-8, which receives the position signal with the highest intensity in all of the receiving antennas. The switch control block 31b determines the direction of the specified receiving antenna with respect to the center O of the relative position detector 37d as a direction of the position signal transmitter 38, in other words, a direction of the operator OP.

Specifically, as shown in FIG. 3C, it is assumed that the position signal transmitter 38 fitted to the operator OP is located in, for example, the directional receiving pattern P-8 of the receiving antenna 37d-8. In FIG. 3C, a reference numeral of 38-1 is assigned to the position signal transmitter 38.

In this assumption, the position signal transmitted from the position signal transmitter 38-1 is received by the receiving antennas 37d-1 to 37d-8 of the relative position detector 37d, respectively. The intensities of the received position signals received by the respective receiving antennas 37d-1 to 37d-8 are compared with one another by the switch control block 31b, thereby specifying that the receiving antenna 37d-8 detects the receiving signal having the highest intensity in all of the receiving antennas 37d-1 to 37d-8. This allows the switch control block 31b to recognize that the position signal transmitter 38-1 is in the diagonally lower left direction from the center O in FIG. 3C, which corresponds to the direction of the receiving antenna 37d-8 with respect to the center O. In other words, the switch control block 31b recognizes that the foot switch 37 is located in the diagonally upper right direction from the position signal transmitter 38-1 (the operator OP).

As another example, as shown in FIG. 3C, it is supposed that the position signal transmitter 38 fitted to the operator OP is located in, for example, the directional receiving pattern P-2 of the receiving antenna 37d-2. In FIG. 3C, a reference numeral of 38-2 is assigned to the position signal transmitter 38.

In another example, the position signal transmitted from the position signal transmitter 38-2 is received by the receiving antennas 37d-1 to 37d-8 of the relative position detector 37d, respectively. The intensities of the position signals received by the respective receiving antennas 37d-1 to 37d-8 are compared with one another by the switch control block 31b, thereby determining that the receiving antenna 37d-2 detects the receiving signal having the highest intensity in all of the receiving antennas 37d-1 to 37d-8. This permits the switch control block 31b to recognize that the position signal transmitter 38-2 is located in the diagonally lower right direction from the center O in FIG. 3C, which corresponds to the direction of the receiving antenna 37d-2 with respect to the center O. That is, the switch control block 31b recognizes that the foot switch 37 is located in the diagonally upper left direction from the position signal transmitter 38-2 (the operator OP).

In order to provide a particular way of estimating a distance of the position signal transmitter 38 from the relative position detector 37d as the relative position information of the position signal detector 38, it is assumed that the receiving antenna 37d-1 receives the position signal having the highest intensity in all of the receiving antennas 37d-1 to 37d-8.

In this assumption, the switch control block 31b compares the intensity of the received position signal by the receiving antenna 37d-1 with a reference value indicative of a reference intensity that has a predetermined relationship with respect to a corresponding given distance. The switch block 31b estimates the distance between the position signal transmitter 38 and the relative position detector 37d based on the comparison result.

When the relative position information between the foot switch 37 and the operator OP (the position signal transmitter 38 and the relative position detector 37d) is transmitted from the switch control block 31b, the display control block 31a has a third function of receiving the transmitted relative position information. The display control block 31a, as the third function, performs control processes to convert the received relative position information into a visual configuration that the operator OP can visually recognize, thereby displaying the converted visual configuration of the received relative position information on the display's screen in collaboration with a third function of the display 32.

Next, overall operations of the medical system 30 according to the first embodiment will be described hereinafter.

Particularly, in the first embodiment, (1) overall operations of the medical system 30 to select one of the therapeutic treatment devices according to the operation of the foot switch 37 by the operator OP will be described hereinafter. In addition, (2) overall operations of the medical system 30 to detect the position of the foot switch 37 in a case where the operator OP loses the position of the foot switch 37 while using the selected therapeutic treatment device to treat the surgical field of the patient P will be described hereinafter.

(1) Selection of one of the therapeutic treatment devices due to either the operator's control of the foot switch 37 or speech-input through the microphone 31g It is supposed that the endoscope image 32a of the patient P lain on the operating table T, which is taken by the electric endoscopic device 33, is displayed on the screen of the display 32 under the control of the medical system controller 31.

In this supposition, the operator OP investigates the endoscope image 32a displayed on the display's screen to closely observe the surgical field of the patient P. This allows the operator OP to determine one of the therapeutic treatment devices and its operating mode (for example, the ultrasonic therapeutic device 34 and 70% output as the operating mode), which match the state of the surgical field.

After the determination, the operator OP operates to turn the selection switch 37c on one or more times for selecting and specifying the ultrasonic therapeutic device 34 and its operating mode of 70% output.

In response to the turning-on operations of the selection switch 37c, the above processes of the selection switch 37c, the switch control block 31b, and the display control block 31a are performed. This results in that the selection images 32b representing the selected therapeutic treatment devices and their operating modes, respectively, are switchably displayed on the screen of the display 32 every operation of the operator's selection switch 37c.

The operator OP watches the switchably displayed selection images 32b. When the operator visually recognizes that the operator's desired selection image 32b representing the ultrasonic therapeutic device 34 and its operating mode of 70% output is displayed on the display's screen, the operator OP operates to turn the output switch 37a of the foot switch 37 on and to keep the on state of the output switch 37a.

This turning-on operation and keeping operation of the output switch 37a permit the output switch 37a, the switch control block 31b and the like to transmit, to the ultrasonic therapeutic treatment device 34, the operational instruction information for causing the selected ultrasonic therapeutic treatment device 34 to operate in the selected operating mode of 70% output.

The ultrasonic therapeutic treatment device 34 receives the transmitted operational instruction information to be driven in the operating mode of 70% output based of the received operational instruction information. As a result, the operator OP uses the operator's specified therapeutic treatment device driven in the operator's specified operating mode to treat the surgical field of the patient P.

While using the specified therapeutic treatment device driven in the specified operating mode, the selection image 32b representing the specified therapeutic treatment device and its operating mode is displayed on the screen of the display 32. This allows the operator OP to visually recognize the operator's selected therapeutic treatment device and the operator's selected operating mode, making it possible to check the selected device and the selected operating mode at any time during the turning-on of the output switch 37a.

In the first embodiment, the operator OP can produce a speech indicative of the identifier of the specified device, for example, the identifier of the ultrasonic therapeutic treatment device 34 and its operating mode of, for example, 70% output. The produced speech indicative of the selection information is processed by the microphone 31g and the speech input block 31d set forth above so as to be transmitted to the switch control block 31b and the display control block 31a, respectively.

This results in that the selection image 32b representing the specified therapeutic treatment device and its specified operating mode by the speech input is displayed on the screen of the display 32. As a result, the turning-on operation and keeping operation of the output switch 37a allow the specified therapeutic treatment device, such as ultrasonic therapeutic treatment device 34, to be driven in the specified operating mode, such as 70% output.

After the treatment with respect to the surgical field of the patient P under the operations of the ultrasonic therapeutic treatment device 34 is completed, the operator OP operates to turn the on-state output switch 37a off. This turning-off operation of the output switch 37a causes the switch control block 31b to transmit the turning-off instruction information to the specified ultrasonic therapeutic treatment device 34, making it possible to turn the operation of the ultrasonic therapeutic treatment device 34 off.

As described above, the medical system 30 according to the first embodiment allows the operator OP to easily and rapidly specify, with the use of the foot switch 37 and/or the microphone 31g, one of the therapeutic treatment devices and its operating mode. The specified therapeutic treatment device and its operating mode match the state of the patient's surgical field while visually investigating the endoscope image 32a of the surgical field. Furthermore, the medical system 30 according to the first embodiment allows the operator OP to easily and rapidly give the operational instruction information (turning-on or turning-off instruction information), with the use of the foot switch 37 and/or the microphone 31g, to the specified therapeutic treatment device.

(2) Detection of the position of the foot switch 37

As described in the overall operations of the (1) "Selection of one of the therapeutic treatment devices", when determining one of the therapeutic treatment devices and its operating mode that match the surgical field of the patient P, the operator OP tries to operate the foot switch 37 to specify the determined therapeutic treatment device and its operating mode. In particular, the operator OP tries to push the operator's foot down on the selection switch 37c.

In this situation, when the operator OP does not find the foot switch 37, the operator OP produces a speech indicative of a keyword, such as "foot switch" for providing an operational instruction to the control unit 31U through the microphone 31g. The aim of the operational instruction is to cause the control unit 31U to detect the position of the foot switch 37.

The produced keyword "foot switch" is inputted to the microphone 31g to be converted into a speech signal. The speech signal is amplified by the microphone 31g to be supplied to the speech input block 31d.

The speech input block 31d receives the supplied speech signal to perform speech recognition based on the speech signal, thereby recognizing the keyword of "foot switch". The speech input block 31d provides the speech recognition information indicative of the keyword of "foot switch" to the switch control block 31b.

The switch control block 31b operates in a foot switch's position searching mode in response to receiving the speech recognition information indicative of "foot switch". In the foot switch's position searching mode, the switch control block 31b is adapted to control the operation of the relative position detector 37d through the switch input block 31c, thereby causing the relative position detector 37d to receive the position signals transmitted from the position signal transmitter 38. In the foot switch's position searching mode, the switch control block 31b is also adapted to detect the relative positional relationship between the position signal transmitter 38 and the relative position detector 37d based on the received position signals.

The operations of the control unit 31U in the foot switch's position searching mode will be described with reference to FIG. 4. The flowchart shown in FIG. 4 represents processes of the functional blocks 31a to 31e of the control unit 31U in accordance with the program codes installed in the control unit 31U.

That is, when the operator OP produces the speech indicative of the keyword of "foot switch" for searching the position of the foot switch 37, the produced speech of "foot switch" is converted by the microphone 31g into the speech signal so as to be amplified thereby. The amplified speech signal is supplied to the control unit 31U.

Figure 4:
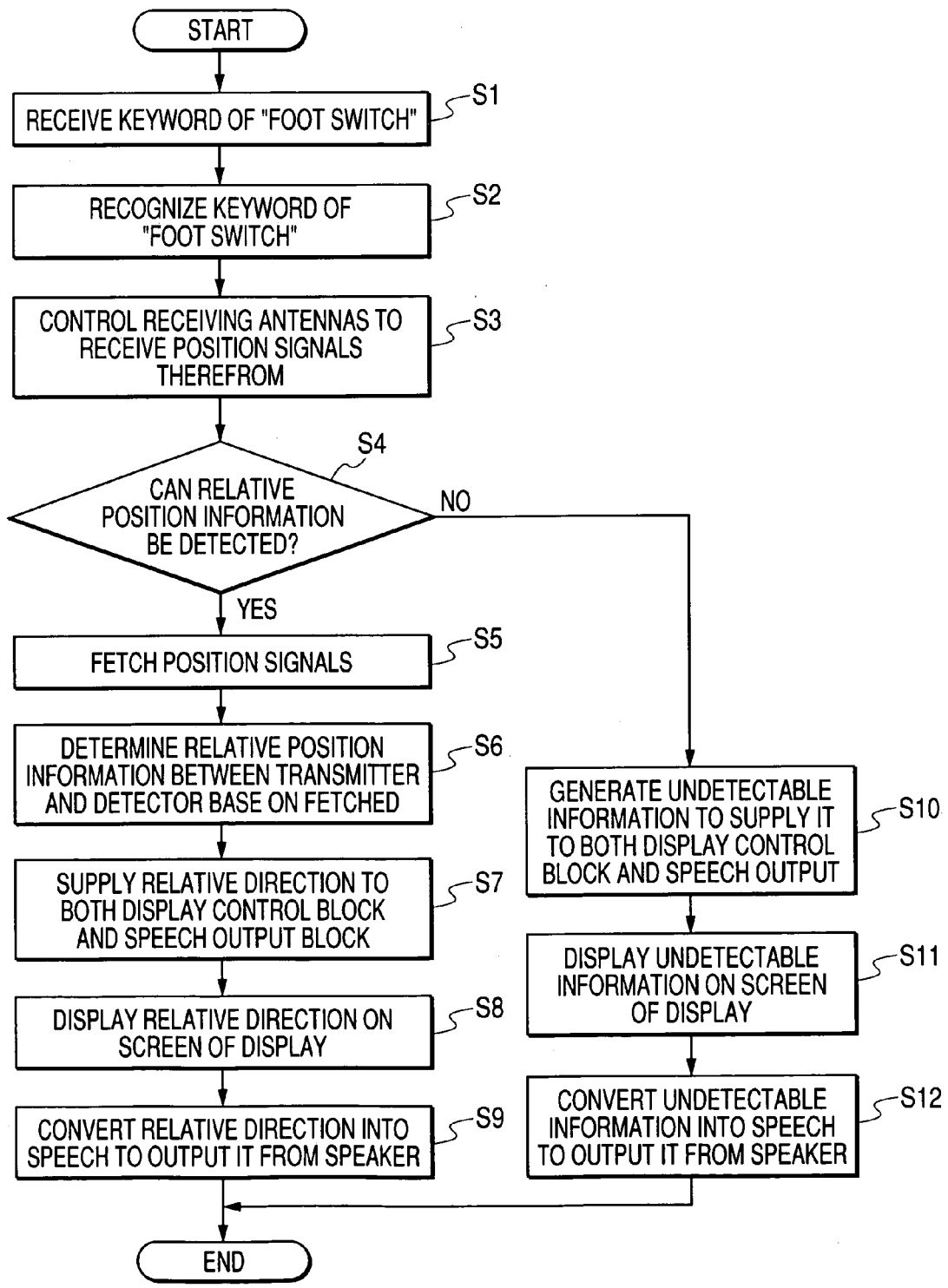
FIG. 4 is a flow chart schematically illustrating an example of operations of a control unit shown in FIG. 2.

The speech input block 31d of the control unit 31U receives the supplied speech signal in step S1 of FIG. 4 to perform speech recognition based on the speech signal, thereby recognizing the keyword of "foot switch" in step S2.

In step S3, the switch control block 31b of the control unit 31U controls the operations of all of the receiving antennas 37d-1 to 37d-8 of the relative position detector 37d through the speech input block 31c in response to receiving the speech-recognized keyword of "foot switch". The control process causes the receiving antennas 37d-1 to 37d-8 to receive the position signals transmitted from the position signal transmitter 38, respectively.

Subsequently, the switch control block 31b determines whether the position signals are transmitted from more than a predetermined number of receiving antennas out of the receiving antennas 37d-1 to 37d-8. In other words, the switch control block 31b determines whether the block 31b can obtain the relative position information between the position signal transmitter 38 and the relative position detector 37d in step S4.

When the position signals are transmitted from more than the predetermined number of receiving antennas out of the receiving antennas 37d-1 to 37d-8, the determination in step S4 is YES, so that the switch control block 31b fetches the position signals transmitted from the receiving antennas 37d-1 to 37d-8 through the switch input block 31c in step S5. The switch control block 31b determines the relative position information between the position signal transmitter 38 and the relative position detector 37d based on the fetched position signals in step S6.

An example of the determination processes of the switch control block 31b in step S6 will be explained with reference to FIG. 5.

The switch control block 31b receives the position signals transmitted from, for example, all of the receiving antennas 37d-1 to 37d-8 through the switch input block 31c in step S6a1 of FIG. 5. The switch control block 31b compares the intensities of the position signals corresponding to the receiving antennas 37d-1 to 37d-8 with one another to specify one of the receiving antennas 37d-1 to 37d-8, which receives the position signal having the highest intensity in other receiving antennas in step S6a2.

The switch control block 31b determines a relative direction of the center O of the relative position detector 37d with respect to the specified receiving antenna to obtain a relative direction of the foot switch 37 with respect to the position signal transmitter 38 (the operator OP) based on the determined relative direction of the center O of the relative position detector 37d as the relative position information in step S6a3.

For example, supposing that the receiving antenna receiving the position signal having the highest intensity is the receiving antenna 37d-4, the switch control block 31b recognizes that the relative direction of the foot switch 37 with respect to the position signal transmitter 38 (operator OP) is a diagonally lower left direction.

The switch control block 31b supplies the obtained relative direction as the relative position information to the display control block 31a and the speech output block 31e, respectively, in step S7.

The display control block 31a converts the supplied relative position as the relative position information into a visual configuration that the operator OP can visually recognize, such as an arrow marker or character data indicative of the relative direction. The display control block 31a superimposes the converted visual configuration of the relative direction on the selection image 32b to display them together on the screen, or displays the converted visual configuration of the relative direction on the screen so as to be close to the selection image 32b displayed thereon in step S8.

Figure 6A:
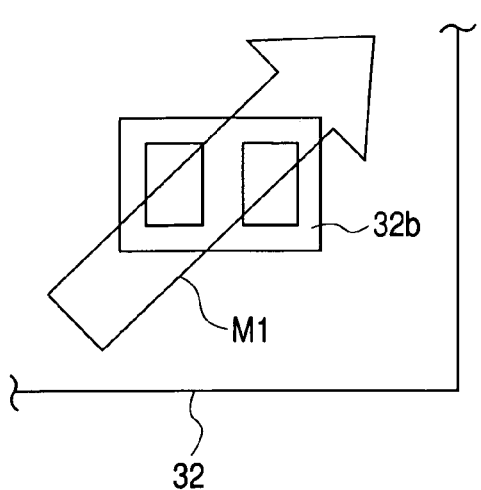
FIG. 6A is an enlarged view schematically illustrating an example of a visual configuration indicative of a relative direction on a screen of a display shown in FIG. 2.

For example, it is supposed that the relative direction between the position signal transmitter 38 and the relative position detector 37d of the foot switch 37 represents that "the foot switch 37 is in the diagonally upper right direction from the position signal transmitter 38 (the operator OP)". In this supposition, the processes of the display control block 31a provide that a transparent arrow marker M1 indicative of the relative direction (the diagonally upper right direction) is superimposed on the selection image 32b displayed on the screen (see FIG. 6A).

Figure 6B:
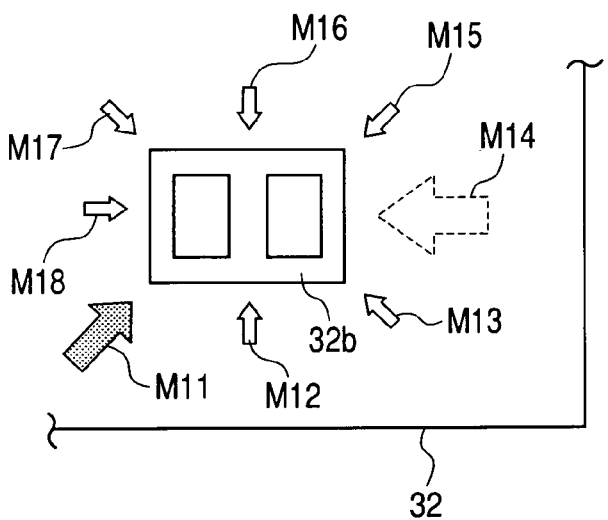
FIG. 6B is an enlarged view schematically illustrating another example of a visual configuration indicative of a relative direction on a screen of a display shown in FIG. 2.

Similarly, it is supposed that the relative direction between the position signal transmitter 38 and the relative position detector 37d of the foot switch 37 represents that "the foot switch 37 is in the diagonally upper right direction from the position signal transmitter 38 (the operator OP)". In this supposition, the processes of the display control block 31a provide that a number of, for example, eight inward arrow markers M11 to M18, which are lightable, respectively, are displayed on the screen around the selection image 32b at substantially constant intervals. The processes of the display control block 31a allow one of the arrow markers M11 to M18, which corresponds to the "diagonally upper right", such as the arrow marker M11, to be turned on (see FIG. 6B). In FIG. 6B, the lighted marker M11 is illustrated to be blacked out.

Furthermore, assuming that the relative direction between the position signal transmitter 38 and the relative position detector 37d represents that "the foot switch 37 is in the left direction from the position signal transmitter 38 (the operator OP)", the processes of the display control block 31a allow one of the arrow markers M11 to M18, which corresponds to the "left direction", such as the arrow marker M14, to be turned on (see FIG. 6B). In FIG. 6B, the lighted marker M14 is illustrated by broken lines.

The control of the visual configuration of one arrow marker that represents the relative position information between the position signal transmitter 38 and the relative position detector 37d is not limited to the control of lighting of the one arrow marker. That is, controlling the visual configuration of one arrow marker that represents the relative position information between the position signal transmitter 38 and the relative position detector 37d to allow the one arrow marker to be visually identified in all of the arrow markers.

Concurrently with the processes in step S8, the speech output block 31e converts the relative direction as the relative position information supplied from the switch control block 31b into speech information recognizable by the operator OP, thereby outputting the converted speech information through the speaker 31f in step S9.

For instance, it is assumed that the relative direction of the foot switch 37 (the relative position detector 37d) with respect to the position signal transmitter 38 indicates that "the foot switch 37 is in the diagonally upper right direction from the position signal transmitter 38 (the operator OP)". In this assumption, the processes of the speech output block 31e allow a speech indicative of the relative direction of the foot switch 37, such as "the foot switch is located in the diagonally upper right direction", to be outputted from the speaker 31f.

On the other hand, when no position signals are transmitted from the receiving antennas 37d-1 to 37d-8 or the position signals are transmitted from not more than the predetermined number of receiving antennas out of the receiving antennas 37d-1 to 37d-8, the determination in step S4 is NO. The switch control block 31b generates undetectable information of relative positional relationship representing that the relative positional relationship between the position signal transmitter 38 and the relative position detector 37d (foot switch 37) is undetectable based on the position signals. The switch control block 31b supplies the generated undetectable information to the display control block 31a and the speech output block 31e, respectively, in step S10.

The display control block 31a converts the contents of the supplied undetectable information from the switch control block 31b into a visual configuration that the operator OP can visually recognize, such as an arrow marker or character data indicative of the undetectable information. The display control block 31a superimposes the converted visual configuration of the undetectable information on the selection image 32b to display them together on the screen, or displays the converted visual configuration of the undetectable information on the screen so as to be close to the selection image 32b displayed thereon in step S11.

Figure 7:
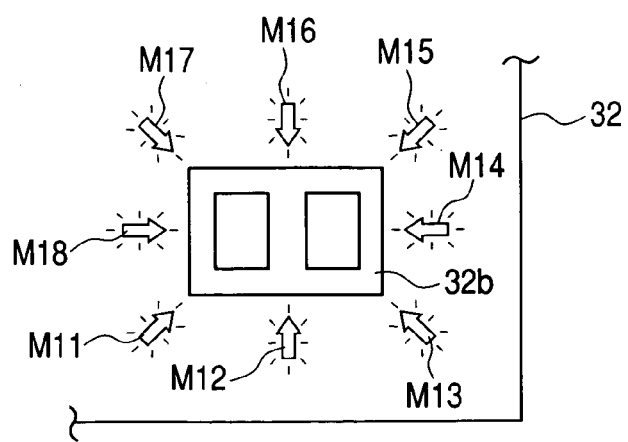
FIG. 7 is an enlarged view schematically illustrating another example of a visual configuration indicative of an undetectable information on a screen of a display shown in FIG. 2.

For example, as shown in FIG. 7, the processes of the display control block 31a allow all of the arrow markers M11 to M18 displayed on the screen around the selection image 32b at substantially constant intervals to blink, respectively. The control of the visual configuration of at least one arrow marker that represents the undetectable information of relative positional relationship between the position signal transmitter 38 and the relative position detector 37d is not limited to the blink of all of the arrow markers.

That is, controlling the visual configuration of at least one arrow marker that represents the undetectable information of relative positional relationship between the position signal transmitter 38 and the relative position detector 37d allows the operator OP to recognize that the relative positional relationship between the position signal transmitter 38 and the relative position detector 37d (foot switch 37) is undetectable based on the position signals.

In parallel with the processes in step S11, the speech output block 31e converts the undetectable information supplied from the switch control block 31b into speech information recognizable by the operator OP, thereby outputting the converted speech information through the speaker 31f in step S12.

For instance, the processes of the speech output block 31e allow a speech indicative of the undetectable information of the foot switch 37, such as "the foot switch is not detected", to be outputted from the speaker 31f.

The processes of the switch control block 31b in step S6 shown in FIG. 5 determine the relative direction as the relative position information. In the first embodiment, in addition to the relative direction, detection of a relative distance between the relative position detector 37d (foot switch 37) and the position signal transmitter 38 (operator OP) becomes possible.

That is, the switch control block 31b executes the processes in step S6a1 and S6a2 shown in FIG. 5, respectively, to identify one receiving antenna corresponding to the position signal having the highest intensity.

Next, the switch control block 31b compares the intensity of the receiving signal received by the identified receiving antenna with the reference value indicative of the reference intensity that has the predetermined relationship with respect to the corresponding given distance. The switch block 31b estimates the relative distance of the foot switch 37 (the relative position detector 37d) with respect to the position signal transmitter 38 based on the comparison result in step S6b1 of FIG. 8.

The switch control block 31b determines whether the estimated relative distance is within a predetermined distance, such as 1 m centered with respect to the operator OP in step S6b2.

When the estimated relative distance is within the predetermined distance, the determination in step S6b2 is YES, so that the switch control block 31b determines a relative direction of the center O of the relative position detector 37d with respect to the specified receiving antenna. The switch control block 31b obtains a relative direction of the foot switch 37 with respect to the position signal transmitter 38 (the operator OP) based on the determined relative direction of the center O of the relative position detector 37d. The switch control block 31b determines the relative position information representing that the relative distance is within the predetermined distance in the obtained relative direction in step S6b3.

On the other hand, when the estimated relative distance exceeds the predetermined distance, the determination in step S6b2 is NO, so that the switch control block 31b determines a relative direction of the center O of the relative position detector 37d with respect to the specified receiving antenna. The switch control block 31b determines a relative direction of the foot switch 37 with respect to the position signal transmitter 38 (the operator OP) based on the determined relative direction of the center O of the relative position detector 37d. The switch control block 31b determines the relative position information representing that the relative distance exceeds the predetermined distance in the obtained relative direction in step S6b4. The switch control block 31b supplies the obtained relative position information to the display control block 31a and the speech output block 31e, respectively (see step S7 of FIG. 4).

The display control block 31a converts the supplied relative position information into a visual configuration visually recognizable by the operator OP, such as an arrow marker or character data. The display control block 31a superimposes the converted visual configuration of the relative position information on the selection image 32b to display them together on the screen, or displays the converted visual configuration on the screen so as to be close to the selection image 32b displayed thereon (see step S8 of FIG. 4).

For example, it is supposed that the relative position information between the position signal transmitter 38 and the relative position detector 37d of the foot switch 37 represents that "the foot switch 37 is in the diagonally upper right direction from the position signal transmitter 38 (the operator OP) and within the predetermined distance". In this supposition, the display control block 31a displays the transparent arrow marker M1 indicative of the relative direction (the diagonally upper right direction) on the selection image 32b (see FIG. 6A) or close to the selection image 32b (see FIG. 6B) so that the size of the arrow marker M1 becomes a predetermined first size representing that the relative distance is within the predetermined distance. For example, when the relative distance between the foot switch 37 and the position signal transmitter 38 is within the predetermined distance, the arrow marker is displayed so that its lateral width gets to be thick and its longitudinal length gets to be short.

The speech output block 31e converts the relative position information supplied from the switch control block 31b into speech information recognizable by the operator OP, thereby outputting the converted speech information through the speaker 31f (see step S9 of FIG. 4).

For example, it is supposed that the relative position information of the foot switch 37 (the relative position detector 37d) with respect to the position signal transmitter 38 indicates that "the foot switch 37 is in the diagonally upper right direction from the position signal transmitter 38 (the operator OP), and the relative distance is within the predetermined distance". In this supposition, the processes of the speech output block 31e allow a speech indicative of the relative position information of the foot switch 37, such as "the foot switch is located in the diagonally upper right direction and close to the operator", to be outputted from the speaker 31f.

In contrast, it is supposed that the relative position information between the foot switch 37 (the relative position detector 37d) and the position signal transmitter 38 indicates that "the foot switch 37 is in the diagonally upper right direction from the position signal transmitter 38 (the operator OP), and the relative distance exceeds the predetermined distance".

In this supposition, the display control block 31a displays the transparent arrow marker M1 indicative of the relative direction (the diagonally upper right direction) on the selection image 32b (see FIG. 6A) or close to the selection image 32b (see FIG. 6B) so that the size of the arrow marker M1 becomes a predetermined second size representing that the relative distance is out of the range of the predetermined distance around the operator OP. For example, when the relative distance between the foot switch 37 and the position signal transmitter 38 is out of the range of the predetermined distance around the operator OP, the arrow marker is displayed so that its lateral width gets to be thin and its longitudinal length gets to be long.

In addition, the speech output block 31e converts the relative position information supplied from the switch control block 31b into speech information recognizable by the operator OP, thereby outputting the speech information through the speaker (see step S9). For example, assuming that the relative position information of the foot switch 37 (the relative position detector 37d) with respect to the position signal transmitter 38 indicates that "the foot switch 37 is in the diagonally upper right direction from the position signal transmitter 38 (the operator OP) and is out of the range of the predetermined distance".

In this assumption, the processes of the speech output block 31e allow a speech indicative of the relative position information of the foot switch 37, such as "the foot switch is located in the diagonally upper right direction at a distance therefrom", to be outputted from the speaker 31f.

As a result, the operator OP recognizes the relative position information displayed on the screen of the display 32 and/or outputted as a speech from the speaker 31f.

This feature allows, even if the operator OP does not find the position of the foot switch 37, the operator OP to easily search and find the position of the foot switch 37 based on the recognized relative position information including at least one of the relative direction and the relative distance of the foot switch 37.

Let us consider a medical system lacking the obtaining function of relative position information and the notification function of relative position information to the operator OP. In this case, when the operator OP does not find the position of the foot switch, the operator OP needs to turn the operator's eyes from the surgical field to the floor of the examining room and/or to blindly move the operator's foot circumferentially to search for the foot switch.

However, the medical system 30 of the first embodiment allows the operator OP to recognize the relative position information while visually investigating the surgical field through the endoscope image 32a displayed on the screen of the display 32. This feature permits the operator OP to move the operator's foot according to the relative position information without turning the operator's eyes from the surgical field and diverting the operator's interest therefrom, making it possible to smoothly detect the foot switch 37.

This results in expediting the selection of one of the therapeutic treatment devices and the treatment of using the selected therapeutic treatment device, thereby improving treatment efficiencies in the medical system 30 of the first embodiment.

Next, let us consider a case where, after the treatment of using the selected therapeutic treatment device, when using another one of the therapeutic treatment devices to treat a surgical field at intervals, the operator OP forgets the previously used therapeutic treatment device so as not to recognize which device and which operating mode are selected.

In this case, however, the medical system 30 of the first embodiment permits the operator OP to visually recognize the selection image 32*b* displayed on the screen of the display 32 to recognize which device and which operating mode are selected at any given time.

Incidentally, in the first embodiment, the relative direction between the foot switch 37 and the position signal transmitter 38 (operator OP) or both the relative direction and the relative distance therebetween are obtained as the relative position information, and the obtained relative position information is notified to the operator OP. In the first embodiment, however, the only relative direction may be notified to the operator OP.

In the first embodiment, the position signal transmitter 38 is operative to continuously or periodically transmit the position signals, but the present invention is not limited to the structure.

For example, the receiving antennas 37*d*-1 to 37*d*-8 of the relative position detector 37*d* can be configured to receiving and transmitting antennas 37*d*-1*a* to 37*d*-8*a*. Each of the receiving and transmitting antennas 37*d*-1*a* to 37*d*-8*a* has a directional transmitting pattern corresponding to each of the directional receiving patterns P-1 to P-8. The receiving and transmitting antennas 37*d*-1*a* to 37*d*-8*a* are operative to transmit drive signals based on the directional transmitting patterns, respectively.

In this modification, the switch control block 31*b* controls the receiving and transmitting antennas 37*d*-1*a* to 37*d*-8*a* through the switch input block 31*c*, thereby causing all of the receiving and transmitting antennas 37*d*-1*a* to 37*d*-8*a* to transmit the drive signals, respectively.

For example, when the position signal transmitter 38 is located in the directional pattern P1, the position signal transmitter 38 receives the transmitted drive signal transmitted from the receiving and transmitting antenna 37*d*-1*a* to transmit the position signals.

As a result, the receiving and transmitting antennas 37*d*-1*a* to 37*d*-8*a* receive the position signal transmitted from the position signal transmitter 38 so that the determination process of the switch control block 31*b* in step S4 is YES, making it possible for the switch control block 31*b* to shift to the processes after the processes in step S4.

In this modification, a time interval from the transmitting timing of the drive signal from at least one of the transmitting and receiving antennas 37*d*-1*a* to 37*d*-8*a* to the receiving timing of the position signal allows the relative distance between the position signal transmitter 38 and at least one of the transmitting and receiving antennas 37*d*-1*a* and 37*d*-8*a* to be determined.

Moreover, in the first embodiment, the switch control block 31*b* of the control unit 31U executes the processes of obtaining the relative position information, but the present invention is not limited to the structure. That is, a processing unit having functions that are substantially identical with those of the switch control block 31*b* may be installed in the foot switch 37, and the processing unit may execute the processes of obtaining the relative position information between the foot switch 37 and the operator OP.

As another modification of the first embodiment, the position signal transmitter 38 may be installed in the foot switch 37, and the relative position detector 37*d* may be separated from the foot switch 37 to be fitted to the operator OP. In another modification, the position signal transmitter 38 attached to the foot switch 37 may be operative to transmit the position signals based on the drive signals transmitted from the switch input block 31*c*.

In the first embodiment, the relative position detector 37*d* and the foot switch 37 may be integrated with each other, but the present invention is not limited to the structure.

Figure 9:
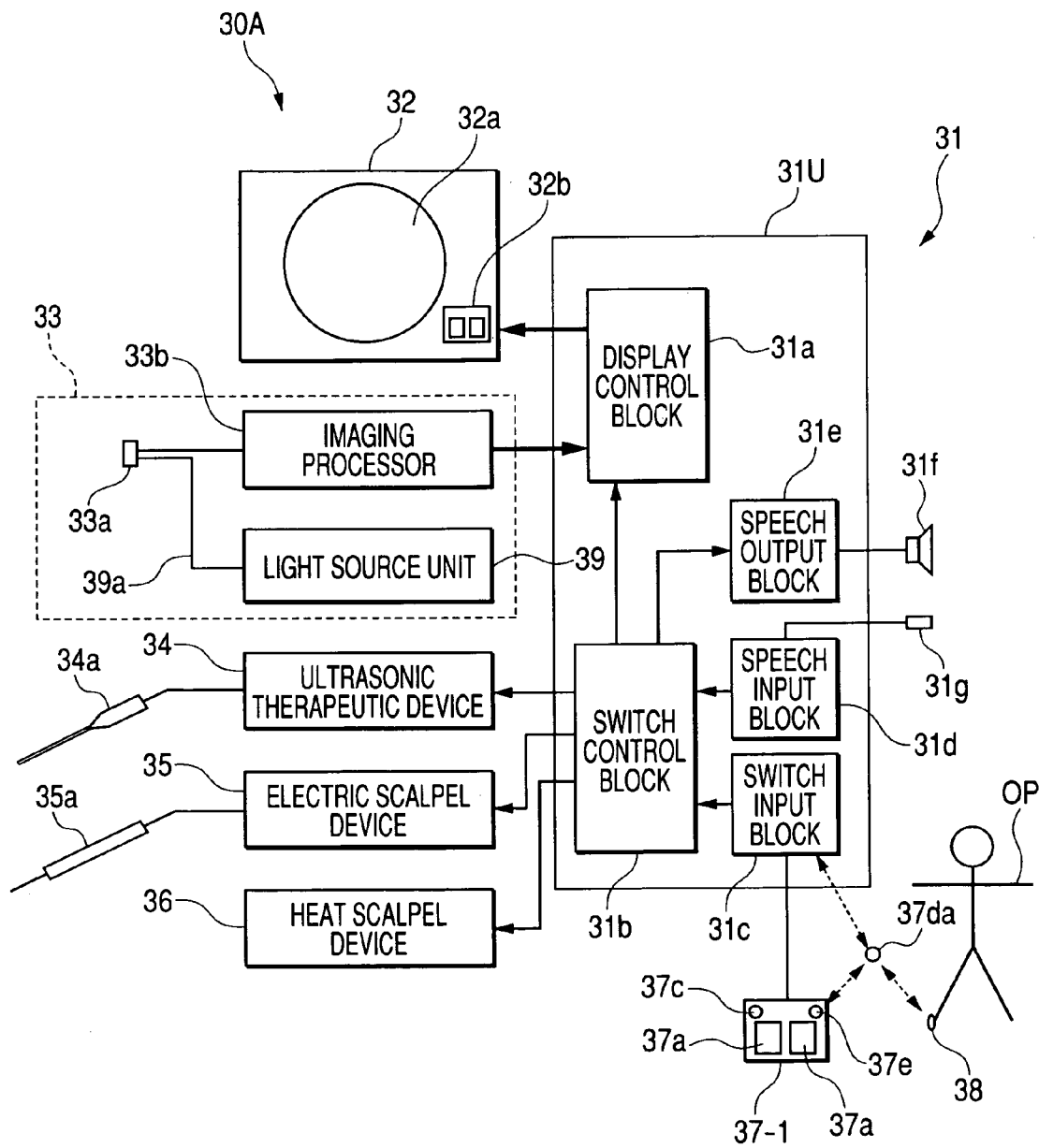
FIG. 9 is a block diagram illustrating a schematic structure of a medical system according to a modification of the first embodiment.

For example, in a medical system 30A shown in FIG. 9, a relative position detector 37*da* is provided independently from a foot switch 37-1. Preferably, the relative position detector 37*da* may be detachable from the foot switch 37-1.

The foot switch 37-1 has a position signal transmitter 37*e* having position signal transmitting functions that are substantially identical with those of the position signal transmitter 38.

That is, each of the receiving antennas 37*d*-1 to 37*d*-8 of the relative position detector 37*da* according to this modification receives position signals transmitted from each of the position signal transmitter 37*e* and the position signal transmitter 38 fitted to the operator OP. Each of the receiving antennas 37*d*-1 to 37*d*-8 supplies the received position signals to the switch input block 31*c*.

The switch control block 31*b* according to the modification, as explained in steps S6 or the like, determines the relative position information of the foot switch 37-1 with respect to the position signal transmitter 37*e* based on the position signals transmitted from the foot switch 37-1. The switch control block 31*b* also determines the relative position information of the position signal transmitter 38 (the operator OP) with respect to the relative position detector 37*da*.

As a result, in this modification, the switch control block 31*b* determines the relative position information between the foot switch 37-1 and the operator OP according to the relative position information between the foot switch 37-1 and the relative position detector 37*da* and that between the operator OP and the relative position detector 37*da*. This feature makes it possible to provide effects that are substantially the same as those in the medical system 30 shown in FIG. 2.

In the first embodiment, one relative position detector 37*d* is attached to the foot switch 37, but the present invention is not limited to the structure.

Figure 10:
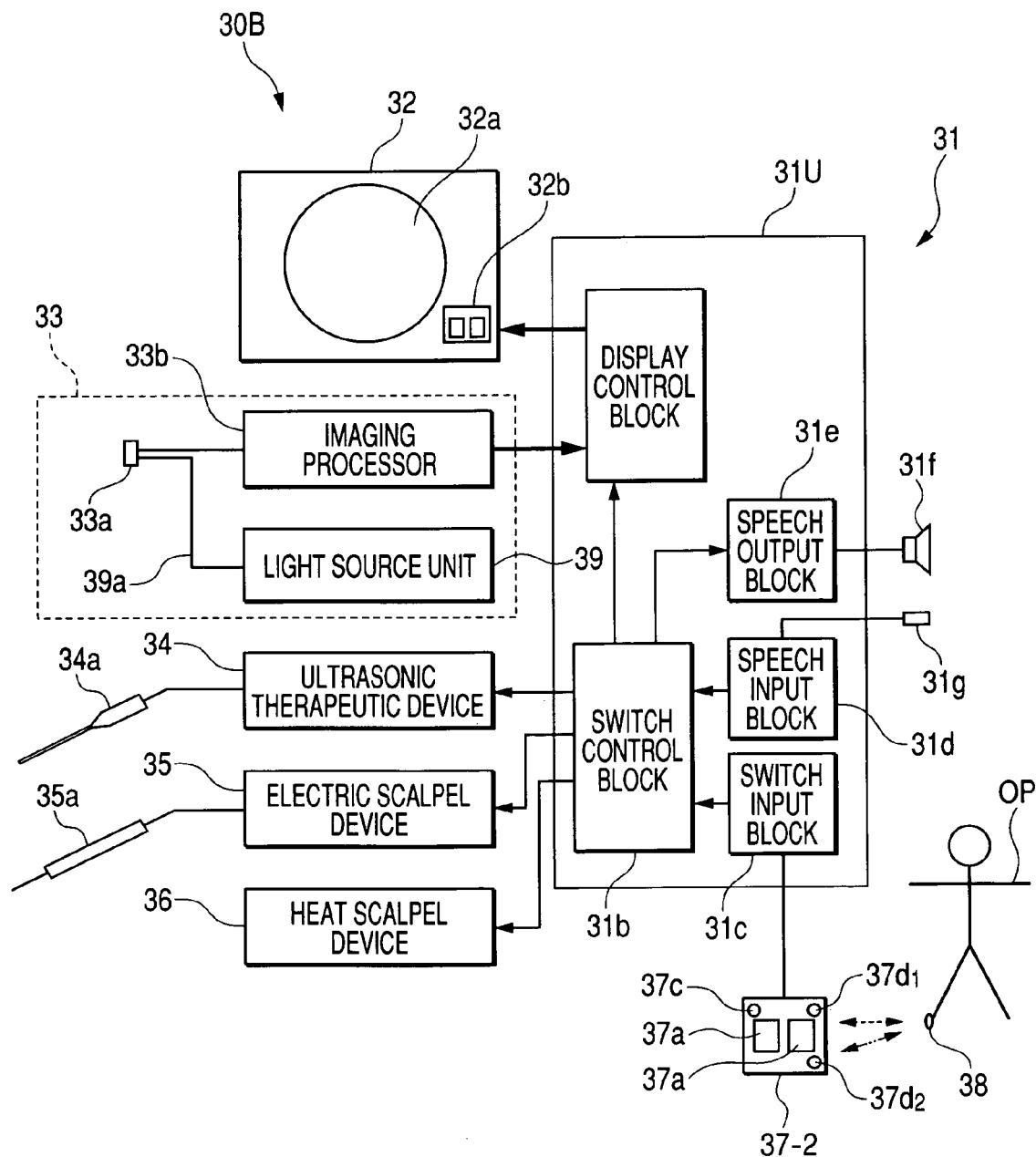
FIG. 10 is a block diagram illustrating a schematic structure of a medical system according to another modification of the first embodiment.

For example, in a medical system 30B shown in FIG. 10, a plurality of, for example, two relative position detectors 37*d*1 and 37*d*2 are attached at predetermined different positions of a foot switch 37-2, respectively.

In this modification, the position signals transmitted from the position signal transmitter 38 are received to the relative position detectors 37*d*1 and 37*d*2, respectively. The position signals are supplied from the relative position detectors 37*d*1 and 37*d*2 to the switch control block 31*b* through the switch input block 31*c*, respectively.

That is, the switch control block 31 b according to this modification determines the relative position information between the foot switch 37-2 and the position signal transmitter 38 by triangulation based on the position signals supplied from the relative position detectors 37*d*1 and 37*d*2. This causes the accuracy of the determined relative position information to be further improved in addition to the effects provided by the medical system 30 shown in FIG. 2.

In the first embodiment, the relative position detector 37*d* having the structure shown in FIGS. 3A to 3C is used as a device for determining information indicative of a relative positional relationship between the foot switch 37 and the operator OP, but the present invention is not limited to the structure. Various types of devices each operative to determine information indicative of a relative positional relationship between the foot switch 37 and the operator OP may be applied in place of the relative position detector 37*d*.

Figure 11B:
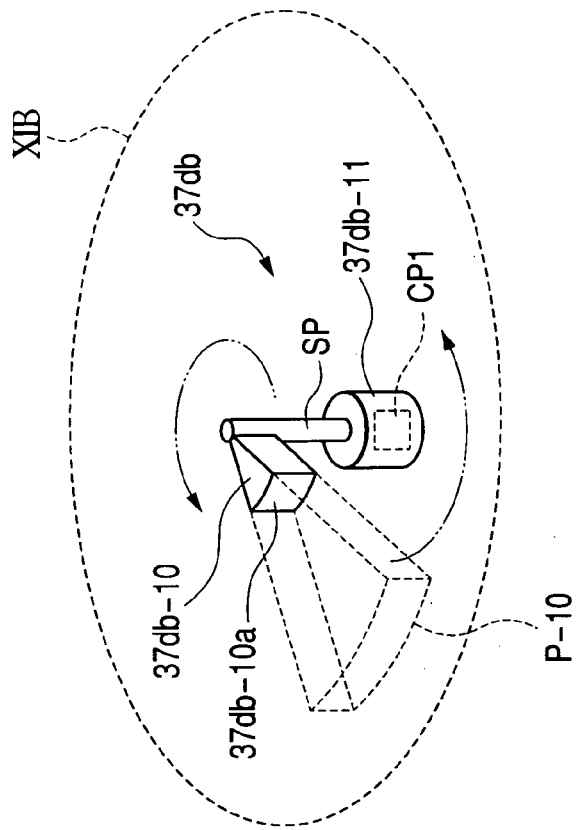
FIG. 11B is an enlarged perspective view schematically illustrating a relative position detector attached to the foot switch shown in FIG. 11A.
Figure 11A:
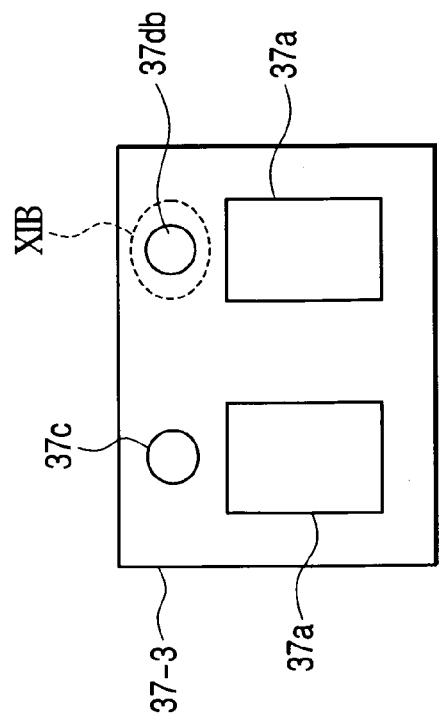
FIG. 11A is a plan view schematically illustrating another example of a foot switch according to the first embodiment.
Figure 11C:
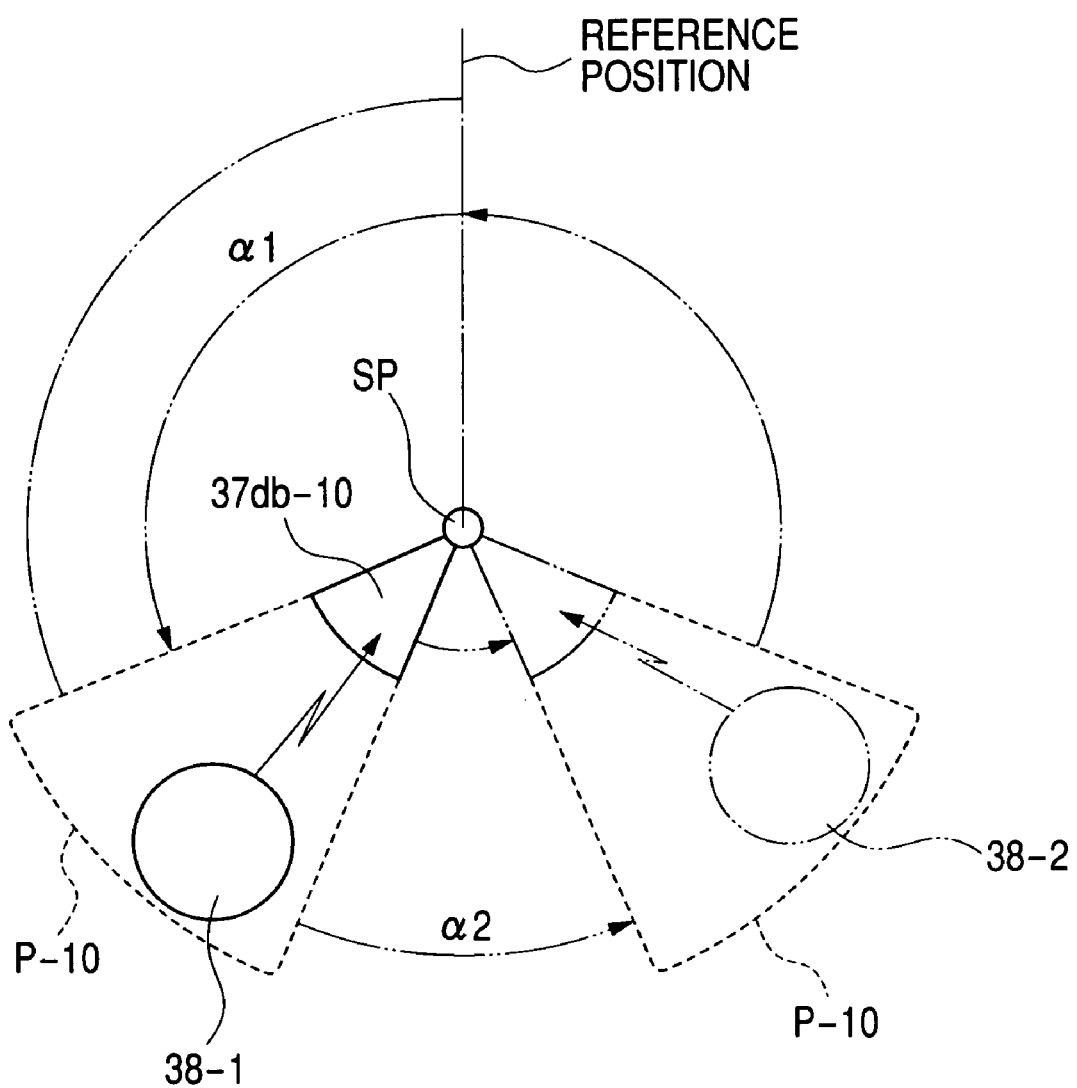
FIG. 11C is an enlarged view schematically illustrating directional receiving patterns of the relative position detector shown in FIG. 11B along a horizontal surface according to the first embodiment.

For example, a relative position detector 37*db* attached to a foot switch 37-3 shown in FIGS. 11A to 11C is provided with a metal receiving antenna 37*db*-10 having a substantially fan-like shape in its cross section parallel to the radial direction. The receiving antenna 37*db*-10 has a receiving directivity in a predetermined direction parallel to, for example, a horizontal surface, such as the floor surface of the examining room.

The fan-like shaped receiving antenna 37db-10 has one circular-arc end surface 37db-10a and the other root end portion. The relative position detector 37db is also provided with a metal supporting pole SP supporting at its one end the root end portion of the receiving antenna 37db-10, and a rotating mechanism 37db-11 supporting the other end of the supporting rod SP. The rotating mechanism 37db-11 causes the supporting pole SP to rotate so that the receiving directivity of the receiving antenna 37db-10 rotates along the horizontal surface within the range of, for example, 360 degrees.

The receiving antenna 37db-10 has a receiving unit operative to receive the position signals each with the predetermined frequency transmitted from the position signal transmitter 38. The receiving antenna 37db-10 also has an amplifier operative to amplify the position signals received by the receiving unit, and an output unit operative to output the amplified position signals.

The receiving antenna 37db-10 has a three-dimensional directional receiving pattern P-10 along the horizontal direction and vertical direction. The directional receiving pattern P-10 has a high sensitivity to some of the position signals transmitted from an area radially extending from the circular-arc end surface 37db-10a of the receiving antenna 37db-10.

The directional receiving pattern P-10 rotating 360 degrees allows the receiving antenna 37db-10 to receive the position signals around the foot switch 37-3.

The rotating mechanism 37db-11 is provided with a comparing unit CP1 operative to hold the position signals outputted from the output unit so as to link the held position signals to corresponding rotation angles (rotation directions) of the receiving antenna 37db-10 from a predetermined reference position, respectively. The comparing unit CP1 is also operative to compare the intensities of the held position signals with one another. The comparing unit CP-1 is communicable with the control unit 31U of the medical system controller 31 by wire cables or radio.

That is, in this modification, the rotating mechanism 37db-11 controls the supporting pole PS based on the drive signal transmitted from the switch input block 31c of the control unit 31U so as to rotate the supporting pole SP. The rotation of the supporting pole SP allows the receiving antenna 37db-10 to rotate together with the supporting pole SP.

The position signals transmitted from the position signal transmitter 38 are received by the rotating receiving antenna 37db-10 for each rotation angle. The position signals received by the receiving antenna 37db-10 are supplied to the comparing unit CP-11.

The intensities of the position signals corresponding to the individual rotation angles of the receiving antenna 37db-10, respectively, are compared with one another. The result of comparison identifies one of the rotation angles at which the position signal having the highest intensity in all of the rotation angles is received by the receiving antenna 37db-10. The identified rotation angle corresponding to a direction with respect to the supporting pole SP provides a relative direction of the position signal transmitter 38, in other words, a relative direction of the operator OP, with respect to the relative position detector 37db.

In particular, as shown in FIG. 11C, it is supposed that, when the receiving antenna 37db-10 is rotated from the reference position at an angle of α1, the position signal transmitter 38 is located in the directional receiving pattern P-10 of the receiving antenna 37db-10 (see a reference numeral of 38-1 assigned to the position signal transmitter 38 in FIG. 11C).

In this supposition, the position signals transmitted from the position signal transmitter 38-1 are received by the rotating receiving antenna 37db-10 for each rotation angle.

The intensities of the position signals corresponding to the individual rotation angles of the receiving antenna 37db-10, respectively, are compared with one another. The result of comparison identifies the rotating angle of α1 at which the position signal having the highest intensity in all of the rotation angles is received by the receiving antenna 37db-10. The comparing unit CP1 recognizes that the position signal transmitter 38-1 is located in a lower left direction in FIG. 11C corresponding to the identified rotation angle of α1 with respect to the supporting pole SP. In other words, the comparing unit CP1 recognizes that the foot switch 37-3 is located in an upper right direction in FIG. 11C corresponding to the opposite direction of the lower left direction determined by the identified rotation angle of α1 with respect to the supporting pole SP.

As another example, assuming that, when the receiving antenna 37db-10 is rotated from the reference position at an angle of α2 so that the position signal transmitter 38 fitted to the operator OP is located in the directional receiving pattern P-10 of the receiving antenna 37db-10 (see a reference numeral of 38-2 assigned to the position signal transmitter 38 in FIG. 11C), the direction of the position signal transmitter 38-2 can be recognized in the same way as the position signal transmitter 38-1.

That is, the comparing unit CP1 recognizes that the position signal transmitter 38-2 is located in a lower right direction in FIG. 11C corresponding to the identified rotation angle of α2 with respect to the supporting pole SP. In other words, the comparing unit CP1 recognizes that the foot switch 37-3 is located in an upper left direction in FIG. 11C corresponding to the opposite direction of the lower right direction determined by the identified rotation angle of α2 with respect to the supporting pole SP.

Furthermore, the comparing unit CP1 compares the intensity of the receiving signal received by the receiving antenna 37db-10 at the identified rotation angle with the reference value indicative of the reference intensity that has the predetermined relationship with respect to the corresponding given distance. The comparing unit CP1 estimates the relative distance of the foot switch 37-3 (the relative position detector 37db) with respect to the position signal transmitter 38 based on the comparison result.

In this modification, the comparing unit CP1 executes the processes of obtaining the relative position information, such as the relative direction and/or the relative distance, but the present invention is not limited to the structure. That is, the switch control block 31b of the control unit 31U may execute the processes of obtaining the relative position information between the foot switch 37 and the operator OP.

In the first embodiment, when using the position signal transmitter capable of transmitting optical position signals as the position signals, such as infrared rays, a relative position detector capable of detecting the optical position signals to convert them into electric signals is needed.

Figure 12A:
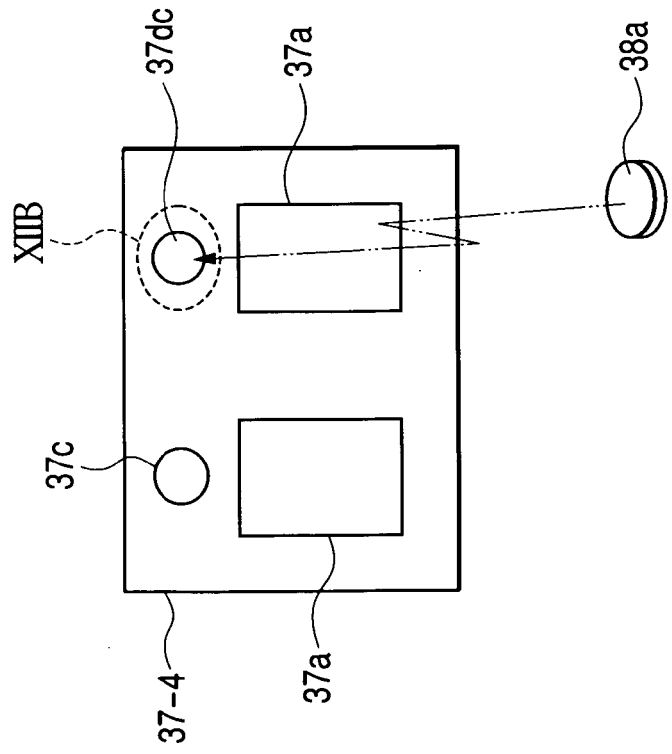
FIG. 12A is a plan view schematically illustrating a further example of a foot switch according to the first embodiment.
Figure 12B:
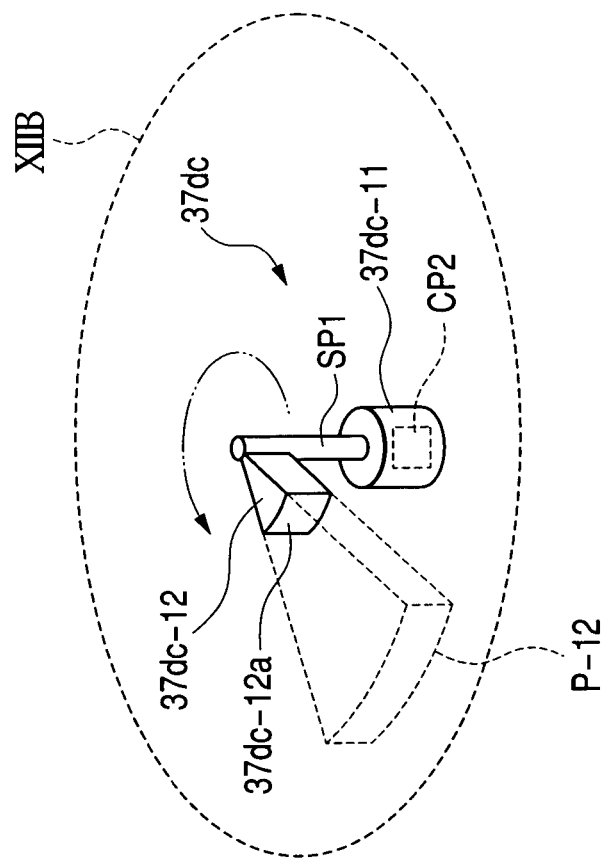
FIG. 12B is an enlarged perspective view schematically illustrating a relative position detector attached to the foot switch shown in FIG. 12A.

As an example of such a relative position detector, a relative position detector 37dc attached to a foot switch 37-4 shown in FIGS. 12A to 12B is provided with a light detecting element 37dc-12 having a substantially fan-like shape in its cross section parallel to the radial direction. The light detecting element 37dc-12 has a receiving directivity in a predetermined direction parallel to, for example, a horizontal surface, such as the floor surface of the examining room.

The fan-like shaped light detecting element 37dc-12 has one circular-arc end surface 37db-12a and the other root end portion. The relative position detector 37dc is also provided with a supporting pole SP1 supporting at its one end the root end portion of the light detecting element 37dc-12, and a rotating mechanism 37dc-11 supporting the other end of the supporting rod SP1. The rotating mechanism 37dc-11 causes the supporting pole SP1 to rotate so that the receiving directivity of the receiving antenna 37dc-12 rotates along the horizontal surface within the range of, for example, 360 degrees.

The light detecting element 37dc-12 has a receiving unit operative to receive the optical position signals transmitted from a position signal transmitter 38a capable of transmitting the optical position signals as the position signals. The light detecting element 37dc-12 also has an amplifier operative to amplify the optical position signals received by the receiving unit, and an output unit operative to convert the amplified optical position signals into electric position signals to output them. Incidentally, the amplification may be executed after the conversion of the optical position signals into the electric position signals.

The light detecting element 37dc-12 has a three-dimensional directional receiving pattern P-12 along the horizontal direction and vertical direction. The directional receiving pattern P-12 has a high sensitivity to some of the optical position signals transmitted from an area radially extending from the circular-arc end surface 37dc-12a of the light detecting element 37dc-12.

The directional receiving pattern P-12 rotating 360 degrees allows the light detecting element 37dc-12 to receive the optical position signals around the foot switch 37-4.

The rotating mechanism 37dc-11 is provided with a comparing unit CP2 operative to hold the optical position signals outputted from the output unit so as to link the held optical position signals to corresponding rotation angles (rotation directions) of the light detecting element 37dc-12 from a predetermined reference position, respectively. The comparing unit CP2 is also operative to compare the intensities of the held optical position signals with one another. The comparing unit CP-12 is communicable with the control unit 31U of the medical system controller 31 by wire cables or radio.

In this modification, the rotating mechanism 37dc-12 controls the supporting pole PS1 based on the drive signal transmitted from the switch input block 31c of the control unit 31U so as to rotate the supporting pole SP1. The rotation of the supporting pole SP1 allows the light detecting element 37dc-12 to rotate together with the supporting pole SP1.

The optical position signals transmitted from the position signal transmitter 38a are received by the rotating light detecting element 37dc-12 for each rotation angle. The optical position signals received by the light detecting element 37dc-12 are supplied to the comparing unit CP-12.

The intensities of the optical position signals corresponding to the individual rotation angles of the light detecting element 37dc-12, respectively, are compared with one another. The result of comparison identifies one of the rotation angles at which the optical position signal having the highest intensity in all of the rotation angles is received by the light detecting element 37dc-12. The identified rotation angle corresponding to a direction with respect to the supporting pole SP1 provides a relative direction of the position signal transmitter 38a, in other words, a relative direction of the operator OP, with respect to the relative position detector 37dc.

Figure 12C:
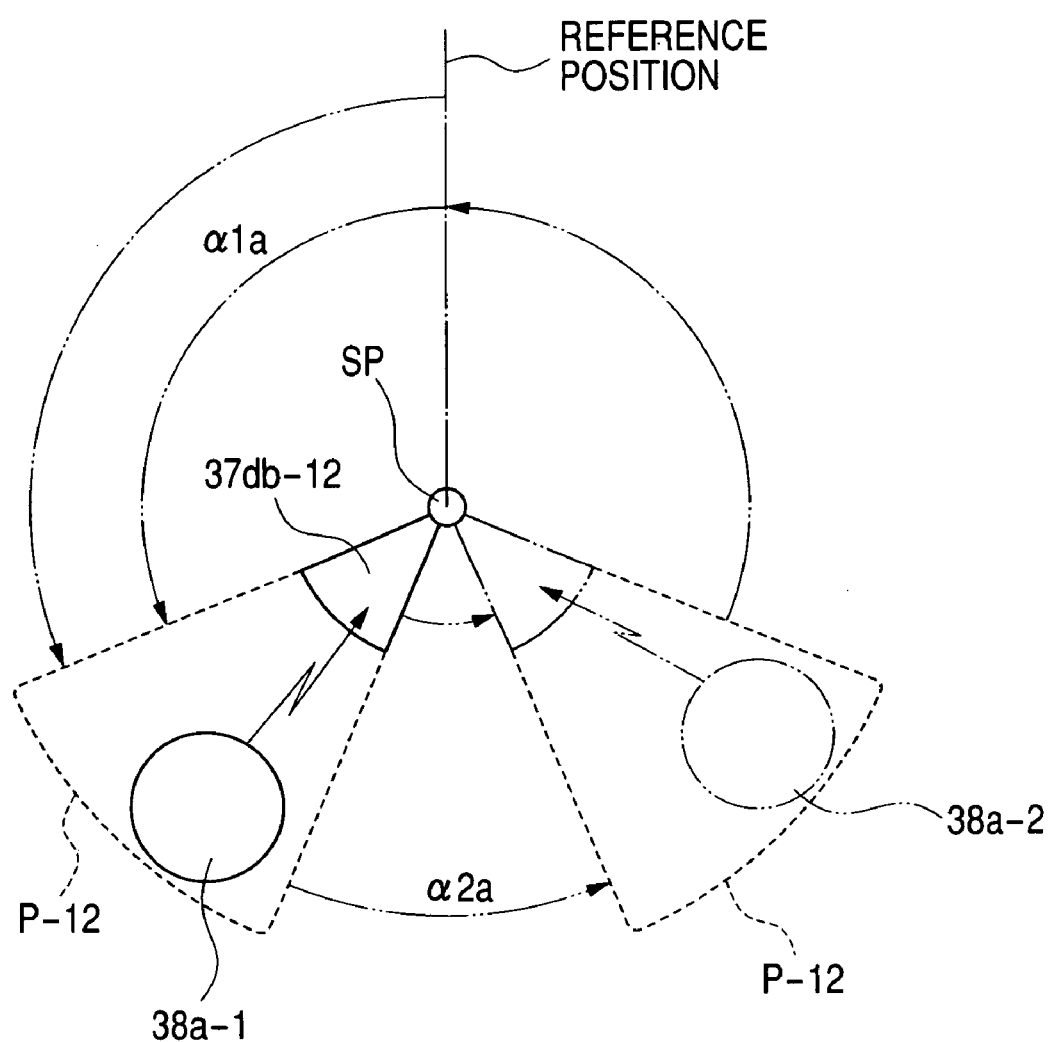
FIG. 12C is an enlarged view schematically illustrating directional receiving patterns of the relative position detector shown in FIG. 12B along a horizontal surface according to the first embodiment.

Particularly, as shown in FIG. 12C, it is supposed that, when the receiving antenna 37dc-12 is rotated from the reference position at an angle of α1a, the position signal transmitter 38a is located in the directional receiving pattern P-12 of the light detecting element 37dc-12 (see a reference numeral of 38a-1 assigned to the position signal transmitter 38a in FIG. 12C).

In this supposition, the position signals transmitted from the position signal transmitter 38a-1 are received by the rotating light detecting element 37dc-12 for each rotation angle.

The intensities of the optical position signals corresponding to the individual rotation angles of the light detecting element 37dc-12, respectively, are compared with one another. The result of comparison identifies the rotating angle of α1a at which the optical position signal having the highest intensity in all of the rotation angles is received by the light detecting element 37dc-12. The comparing unit CP2 recognizes that the position signal transmitter 38a-1 is located in a lower left direction in FIG. 12C corresponding to the identified rotation angle of α1a with respect to the supporting pole SP1. In other words, the comparing unit CP2 recognizes that the foot switch 37-4 is located in an upper right direction in FIG. 12C corresponding to the opposite direction of the lower left direction determined by the identified rotation angle of α1a with respect to the supporting pole SP1.

As another example, assuming that, when the light detecting element 37dc-12 is rotated from the reference position at an angle of α2a so that the position signal transmitter 38a fitted to the operator OP is located in the directional receiving pattern P-12 of the light detecting element 37dc-12 (see a reference numeral of 38a-2 assigned to the position signal transmitter 38a in FIG. 12C), the direction of the position signal transmitter 38a-2 can be recognized in the same way as the position signal transmitter 38a-1.

That is, the comparing unit CP2 recognizes that the position signal transmitter 38a-2 is located in a lower right direction in FIG. 12C corresponding to the identified rotation angle of α2a with respect to the supporting pole SP1. In other words, the comparing unit CP2 recognizes that the foot switch 37-4 is located in an upper left direction in FIG. 12C corresponding to the opposite direction of the lower right direction determined by the identified rotation angle of α2a with respect to the supporting pole SP1.

Furthermore, the comparing unit CP2 compares the intensity of the optical receiving signal received by the light detecting element 37dc-12 at the identified rotation angle with the reference value indicative of the reference intensity that has the predetermined relationship with respect to the corresponding given distance. The comparing unit CP2 estimates the relative distance of the foot switch 37-4 (the relative position detector 37dc) with respect to the position signal transmitter 38a based on the comparison result.

In particular, an optical position signal has a characteristic that the directional range of the intensity of the optical position signal transmitted from the position signal transmitter 38a is easily adjustable to be wide as compared with radio signals. This characteristic allows the comparing unit CP2 to determine the relative positional relationship between the foot switch 37-4 and the operator OP with further accuracy.

Figure 8:
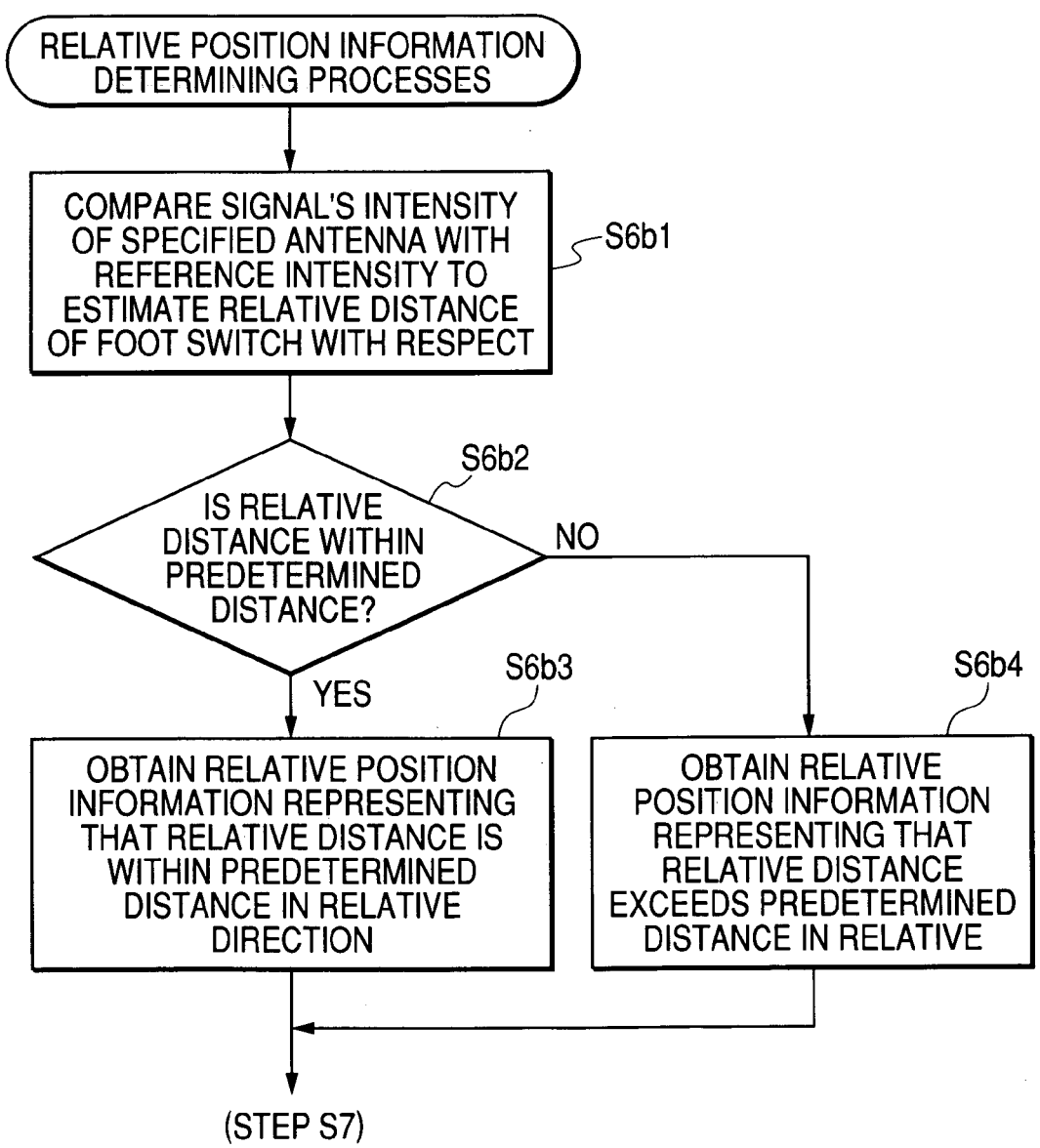
FIG. 8 is a flow chart schematically illustrating an example of operations of a control unit shown in FIG. 2.

In a case of using such a position signal transmitter capable of transmitting optical position signals as the position signals, the eight pieces of receiving antennas 37d-1 to 37d-8 may be replaced with eight pieces of light detecting elements that are arranged like the receiving antennas 37d-1 to 37d-8 shown in FIG. 8. In this modification, comparing the intensities of the optical position signals detected by the eight pieces of light detecting elements with one another permits the relative positional relationship between the foot switch 37-4 and the position signal transmitter 38a to be easily determined.

In the first embodiment, the relative positional relationship between the position signal transmitter and the relative position detector is determined based on the position signals received by the relative position detector, but the present invention is not limited to the structure.

For example, a transmitter attached to the foot switch may be configured to transmit scan signals in a plurality of directions along the horizontal surface on which the operator OP is movable, such as ultrasonic signals. The transmitter may be also configured to receive echo signals reflected from the operator OP and corresponding to the scan signals. A receiver attached to the foot switch may be configured to determine the relative position information between the operator OP and the foot switch in the same ways as the first embodiment.

The medical system according to the first embodiment uses the electronic endoscopic device 33 as one piece of diagnostic monitoring equipment, but the medical system may use another one piece of diagnostic monitoring equipment, such as ultrasonic diagnostic system in place of the electronic endoscopic device 33 or in conjunction with the electronic endoscopic device 33.

In the first embodiment, a direction in which the position signal with the highest intensity in all of the position signals is received is determined as a relative direction of the operator OP with respect to the foot switch, but the present invention is not limited to the structure. For example, all of the received position signals may be weighted based on differences among the intensities of the received position signals, making it possible to estimate the relative positional relationship of the operator OP with respect to the foot switch based on the weighted intensities of the position signals.

In the first embodiment, the control unit 31U (the switch control block 31b) executes the processes shown in FIG. 4 in the foot switch's position searching mode in response to receiving the speech recognition information that is based on the keyword "foot switch" produced by the operator OP and that is supplied through the microphone. The present invention, however, is not limited to the structure.

For example, the control unit 31U may execute the processes shown in FIG. 4 in the foot switch's position searching mode in response to another signal as a trigger, or may periodically or randomly execute the processes shown in FIG. 4 in the foot switch's position searching mode. In these examples, the functional blocks 31d and 31e may be omitted.

In the first embodiment, the control unit 31U is composed of a computer circuit including, for example, at least one microcomputer, but may be composed of a plurality of hardwired circuits that are capable of realizing all of the functions of the functional blocks 31a to 31e.

In addition, the position signal transmitter 38 may be operative to continuously or periodically transmit, as the position signals, directional signals each having a predetermined directivity in a predetermined direction along the horizontal surface. In this structure, the relative position detector has not necessarily individual receiving directivities with respect to the position signals transmitted from the position signal transmitter 38, respectively. Because the position signals each has the predetermined directivity, when the relative position detector receives the position signal, the direction of the position signal transmitted to the relative position detector can be determined as the relative direction of the transmitter 38.

Second Embodiment

Such therapeutic treatment devices explained in the first embodiment have been produced by different manufacturers. For giving operational instructions to each therapeutic treatment device produced by each different manufacturer, each foot switch corresponding to each therapeutic treatment device has also been produced by each different manufacturer.

This may cause the therapeutic treatment devices and the foot switches corresponding thereto, which are produced by the different manufacturers, respectively, to connect to a medical system controller.

The foot switches produced by the different manufacturers do not necessarily have the same specification so that the different manufacturers independently determine specifications of operational instruction signals outputted from their foot switches, respectively.

For using the different foot switches having different specifications, respectively, to construct a medical system, it is necessary, from the different manufacturers, to receive at least the specifications of the operational instruction signals supplied from the different foot switches to the medical system controller.

Checking of whether the received specifications of the operational instruction signals are fitted in combination with the medical system controller are required, and/or setting of the medical system controller to comply with the received specifications of the operational instruction signals are needed.

However, there are many therapeutic treatment devices and many foot switches produced by many different manufacturers in markets so that it is difficult to acquire all specifications of many foot switches produced by many different manufacturers. In addition, it is impractical to design and provide a medical system controller that is fitted to all specifications of many foot switches produced by many different manufacturers.

The second embodiment of the present invention is made to provide a medical system controller allowing the use of a plurality of foot switches having different specifications, respectively, in combination.

Figure 14A:
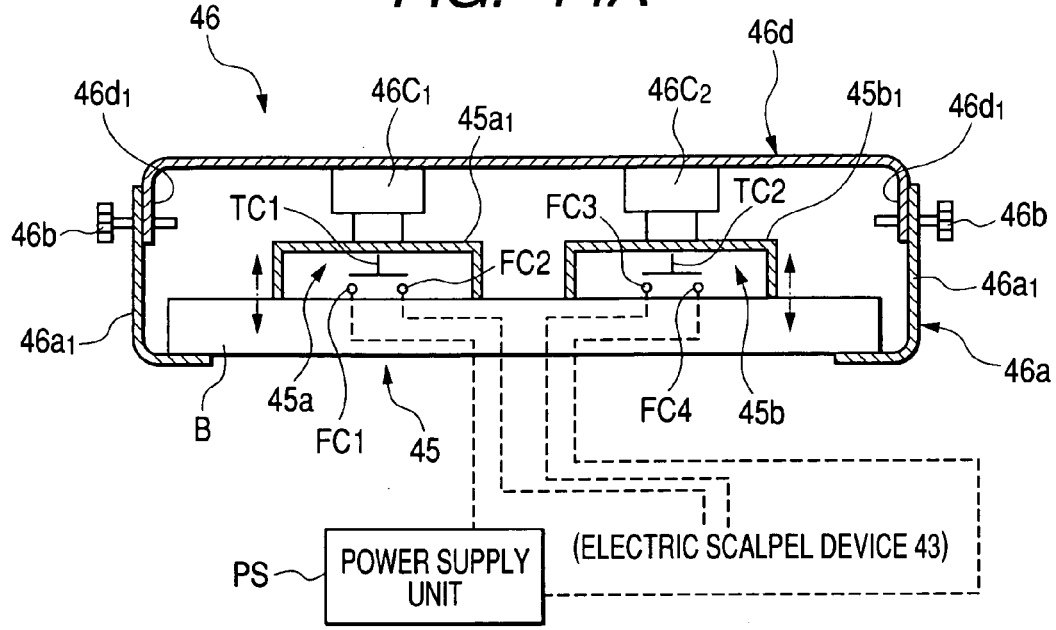
FIG. 14A is a partially cross sectional view illustrating a schematic structure of a foot-switch on-off mechanism shown in FIG. 13.
Figure 14B:
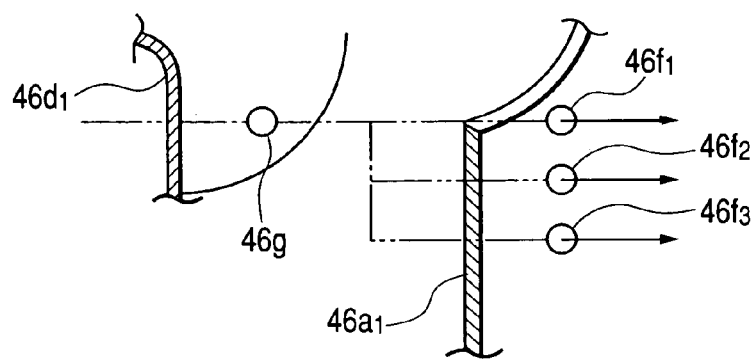
FIG. 14B is a partially enlarged view of the on-off mechanism shown in FIG. 14A.
Figure 14C:
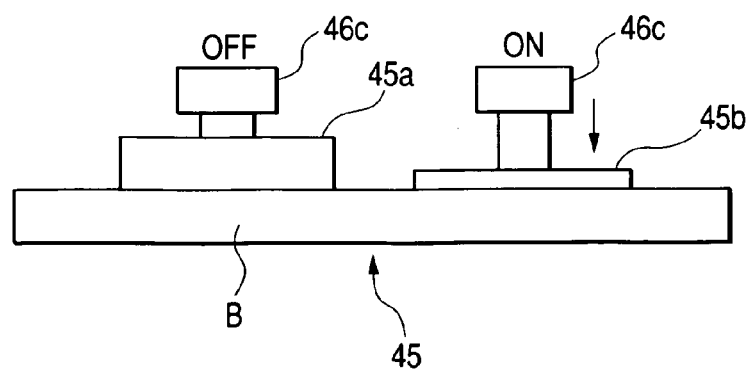
FIG. 14C is a view for explaining operations of the on-off mechanism shown in FIG. 14A.
Figure 15:
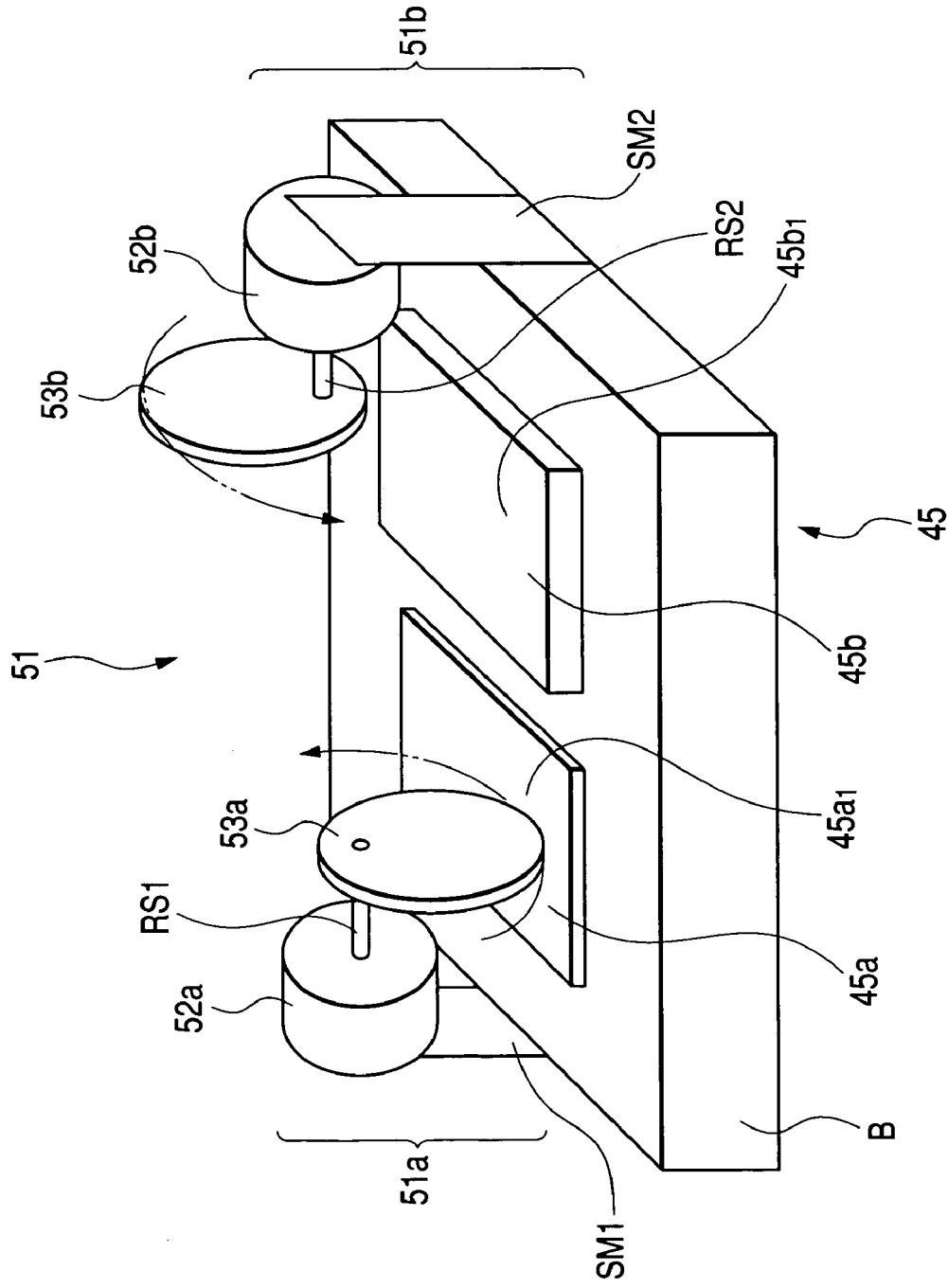
FIG. 15 is an enlarged perspective view illustrating a modification of the on-off mechanism according to the second embodiment of the present invention.

The medical system controller according to the second embodiment will described hereinafter with reference to FIGS. 13 to 15.

Figure 13:
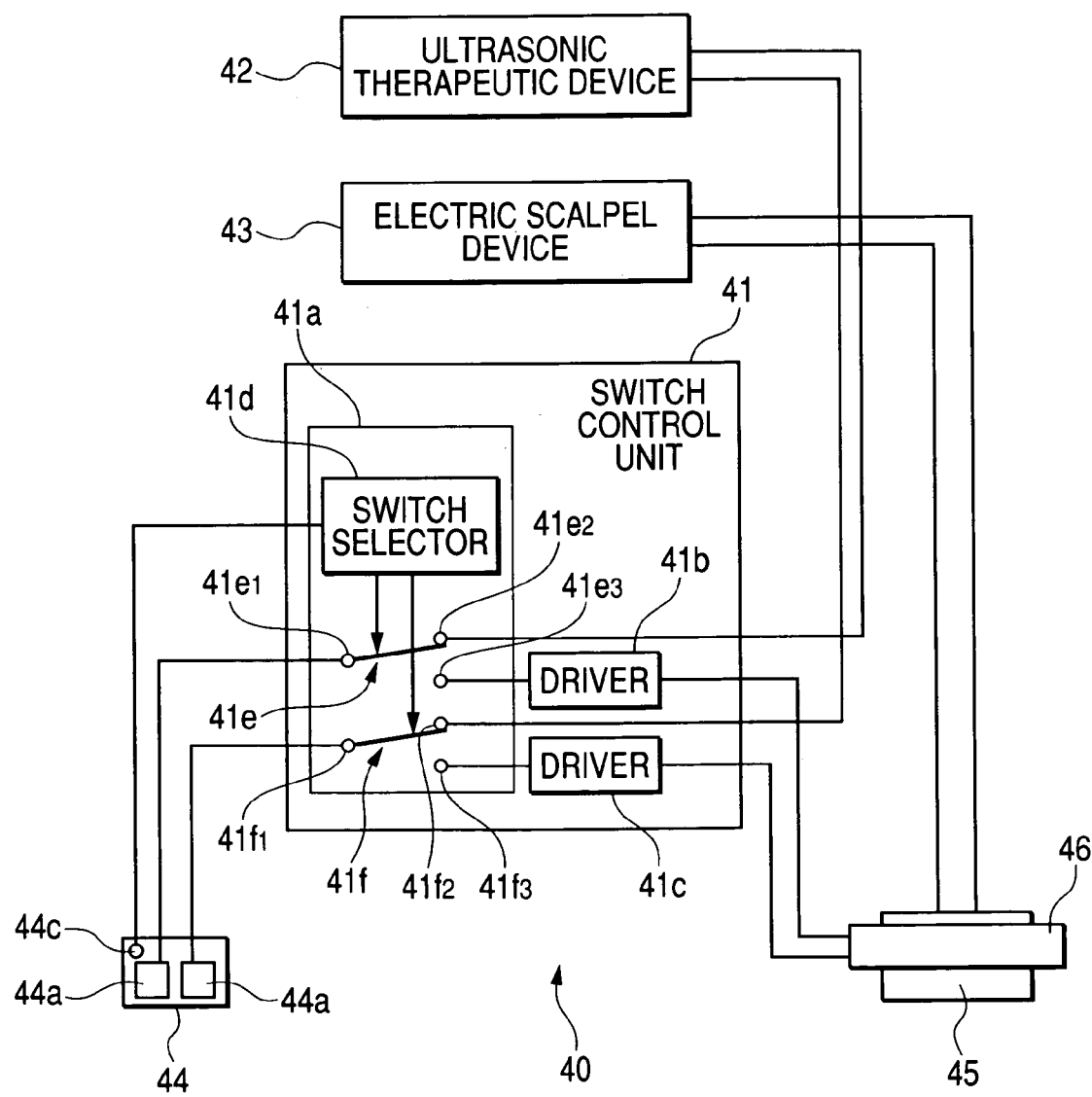
FIG. 13 is a block diagram illustrating a schematic structure of a medical system including a medical system controller according to a second embodiment of the present invention.

FIG. 13 is a block diagram illustrating a schematic structure of a medical system 40 including a medical system controller according to a second embodiment of the present invention. FIG. 14A is a partially cross sectional view illustrating a schematic structure of a foot-switch on-off mechanism shown in FIG. 13. The foot-switch on-off mechanism is referred to simply as "on-off mechanism. FIG. 14B is a partially enlarged view of the on-off mechanism shown in FIG. 14A, and FIG. 14C is a view for explaining operations of the on-off mechanism shown in FIG. 14A.

The medical system 40 using the medical system controller, as shown in FIG. 13, is provided with an ultrasonic therapeutic device 42 and an electric scalpel device 43 as pieces of therapeutic treatment equipment.

The medical system 40 is provided with a first foot switch 44 communicable with the ultrasonic therapeutic device 42 and operative to give operational instructions to the ultrasonic therapeutic device 42, such as turning-on and turning-off instructions. The medical system 40 is provided with a second foot switch 45 communicable with the electric scalpel device 43 and operative to give operational instructions to the electric scalpel device 43, such as turning-on and turning-off instructions.

The ultrasonic therapeutic device 42 and the electric scalpel device 43 are produced by, for example, different manufacturers, respectively. Specifications of parts of the ultrasonic therapeutic device 42 that are related to the first foot switch 44 and those of parts of electric scalpel device 43 that are related to the second foot switch 43 are different from each other. The first and second foot switches 44 and 45 are designed to be produced based on different specifications, respectively.

The medical system controller 41 is communicable with one of the devices 42 and 43, such as the ultrasonic therapeutic device 42 by wire cables or radio. The medical system 40 is provided with the on-off mechanism 46 communicable with the controller 41 by wire cables or radio and mechanically coupled to an on-off switch portion of the second foot switch 45. The on-off mechanism 46 causes the on-off switch portion to be turned on and off.

The controller 41 is composed of a switch control unit 41a, drivers 41b and 41c. The switch control unit 41a has a switch selector 41d, switches 41e and 41f.

The switch selector 41d is electrically connected to the switches 41e and 41f and operative to control switching operations of the switches 41e and 41f, respectively, based on a switching control signal transmitted from the first foot switch 44.

The switch 41e has an input terminal 41e1 to which the on/off operation signals with respect to the ultrasonic therapeutic device 42 are inputted from the first foot switch 44. The switch 41e has an input terminal 41e1 has a first output terminal 41e2 electrically connected through the driver 41b to the ultrasonic therapeutic device 42, and a second output terminal 41e3 electrically connected to the on-off mechanism 46.

The switch 41f has an input terminal 41f1 to which the on/off operation signals with respect to the ultrasonic therapeutic device 42 are inputted from the first foot switch 44. The switch 41f also has a first output terminal 41f2 electrically connected to the ultrasonic therapeutic device 42 and a second output terminal 41f3 electrically connected through the driver 41c to the on-off mechanism 46.

The first foot switch 44, similarly to the first embodiment, has a selection switch 44c and a twin-type output switch 44a. The output of the selection switch 44c is adapted to be supplied to the switch selector 41d of the switch control unit 41a. The output of the output switch 44a is adapted to be supplied to the input terminals 41e1 and 41f1 of the switches 41e and 41f, respectively.

The second foot switch 45 serves as on-off control of the electric scalpel device 43. The second foot switch 45 is adapted to be controlled by the on-off mechanism 46 under the control of the driver 41b or the driver 41c.

The schematic structure of the second foot switch 45 and the on-off mechanism 46 will be explained hereinafter (see FIG. 14A).

The second foot switch 45 is provided with a base portion B substantially having a case shape and an inner follow portion, and one surface (in the second embodiment, bottom surface) and the other surface (in the second embodiment, top surface). The second foot switch 45 is provided with first and second on-off switch members 45a and 45b mounted through the top surface of the base portion B, respectively. The first and second switch members 45a and 45b are individually reciprocable with respect to the inner follow portion of the base portion B along a direction orthogonal to the bottom wall of the base portion B.

The second foot switch 45 has a first movable contact TC1 movable toward the base portion B side together with the move of the first on-off switch member 45a toward the base portion B side. The second foot switch 45 has a first fixed contact FC1 electrically connected to a power supply unit PS, and a second fixed contact FC2 electrically connected to the electric scalpel device 43.

The second foot switch 45 is so configured that the move of the first movable contact TC1 toward the base portion B side allows the first movable contact TC1 to electrically contact to the first and second fixed contacts FC1 and FC2, respectively. This results in that the first movable contact TC1 and each of the first and second fixed contacts FC1 and FC2 are electrically conducted to each other.

These electric conduction between the first movable contact TC1 and each of the first and second fixed contacts FC1 and FC2 allow the power supply unit PS and the electric scalpel device 43 to be electrically conducted to each other so that the electric scalpel device 43 is turned on.

Similarly, the second foot switch 45 has a second movable contact TC2 movable toward the base portion B side together with the move of the second on-off switch member 45b toward the base portion B side. The second foot switch 45 has a third fixed contact FC3 electrically connected to the power supply unit PS, and a fourth fixed contact FC4 electrically connected to the electric scalpel device 43.

The second foot switch 45 is so configured that the move of the second movable contact TC2 toward the base portion B side allows the second movable contact TC2 to electrically contact to the third and fourth fixed contacts FC3 and FC4, respectively. This results in that the second movable contact TC2 and each of the third and fourth fixed contacts FC3 and FC4 are electrically conducted to each other.

These electric conduction between the second movable contact TC2 and each of the third and fourth fixed contacts FC3 and FC4 allows the power supply unit PS and the electric scalpel device 43 to be electrically conducted to each other so that the electric scalpel device 43 is turned on.

Moreover, the second foot switch 45 is so configured that the move of the first movable contact TC1 away from the base portion B side allows the first movable contact TC1 to be separated from the first and second fixed contacts FC1 and FC2, respectively. This results in that the first movable contact TC1 and each of the first and second fixed contacts FC1 and FC2 are electrically separated from each other, whereby the power supply unit PS and the electric scalpel device 43 are electrically separated from each other so that the electric scalpel device 43 is turned off.

Similarly, the second foot switch 45 is so configured that the move of the second movable contact TC2 away from the base portion B side allows the second movable contact TC2 to be separated from the third and fourth fixed contacts FC3 and FC4, respectively. This results in that the second movable contact TC2 and each of the third and fourth fixed contacts FC3 and FC4 are electrically separated from each other, whereby the power supply unit PS and the electric scalpel device 43 are electrically separated from each other so that the electric scalpel device 43 is turned off.

The on-off mechanism 46, as shown in FIGS. 14A to 14C, has a substantially tubular fixing frame 46a made of hard material. The fixing frame 46a has one and the other opening end portions, and a rectangular tubular sidewall portion 46a1. One of the opening end portions is formed with an inward flange. The fixing frame 46a is attached to an outer periphery of the base portion B of the second foot switch 45.

The on-off mechanism 46 is provided with a substantially tubular cover member 46d having one opening end, the other closed end, and a tubular side wall portion 46d1. The cover member 46d is removably attached to the other opening end portion of the fixing frame 46a, and the side wall portion 46d1 is fitted to the other opening end portion of the fixing frame 46a. The opening end of the cover member 46d is located inside the fixing frame 46a.

The on-off mechanism 46 has first and second electromagnetic pistons 46c1 and 46c2 mounted on an inner surface of the other closed end so that the first and second electromagnetic pistons 46c1 and 46c2 are opposite to the first and second on-off switch members 45a and 45b, respectively. The first and second electromagnetic pistons 46c1 and 46c2 are mechanically coupled to the first and second on-off switch members 45a and 45b, respectively.

The first and second electromagnetic pistons 46c1 and 46c2 are electrically connected to the drivers 4b and 41c, respectively, so that the first and second electromagnetic pistons 46c1 and 46c2 are reciprocable with respect to the base portion B based on the drive signals supplied from the drivers 41b and 41c, respectively.

The on-off mechanism 46, as shown in FIG. 14B, has a plurality of screw holes 46f1, 46f2, . . . penetrated through opposing areas of one of the side wall portion 46a1 of the fixing frame 46a and the side wall portion 46d1 of the cover member 46d, respectively. In the first embodiment, the screw holes 46f1, 46f2, . . . are formed at each area of the side wall portion 46a1 so that they are arranged along the reciprocation direction of each piston 46c1, 46c2. The on-off mechanism 46 has at least one screw hole 46g penetrated through each of opposing areas of the other of the side wall portion 46a1 of the fixing frame 46a and the side wall portion 46d1 of the cover member 46d, respectively. In the first embodiment, the fitting hole 46g is formed at each area of the side wall portion 46d1 of the cover member 46d. The screw hole 46g is aligned with one of the screw holes 46f1, 46f2, . . . when the side wall portion 46d1 of the cover member 46d is fitted to the other opening end portion of the fixing frame 46a.

The on-off mechanism 46 has fitting screws 46b. When the side wall portion 46d1 of the cover member 46d is fitted to the other opening end portion of the fixing frame 46a, each of the screw holes 46g is aligned with one of the screw holes 46f1, 46f2, . . . . In this alignment, each of the fitting screws 46b is screwed into each of the screw holes 46g and one of the screw holes 46f1, 46f2, . . . , respectively, which allows the cover member 46d to be fitted to the fixing frame 46a.

That is, in this structure of the on-off mechanism 46, selecting one of the screw holes 46f1, 46f2, . . . into which the fitting screw 46b is screwed allows a positional relationship between each of the first and second pistons 46c1 and 46c2 and each of pressed surfaces 45a1 and 45b1 of the first and second on-off switches 45a and 45b to be adjusted.

The screw holes 46f1, 46f2, . . . , 46g, and fitting screw 46b constitute a positional relationship adjusting mechanism, for example.

Next, operations of the controller 41 and the on-off mechanism 46 will be described hereinafter.

The operator OP of the selection switch 44c of the first foot switch 44 permits the electric connection to the output switch 44a of the first foot switch 44 to be switched between the ultrasonic therapeutic device 43 and each of the driver 41b, 41c.

That is, when the operator OP operates the selection switch 44c of the first foot switch 44 to select the electric scalpel device 43, the switch control signal based on the selection is supplied to the switch selector 41d.

The switch selector 41d switches the electric connection of the first input terminal 41e1 of the switch 41e and the first input terminal 41f1 of the switch 41f from the first output terminals 41e2 and 41f2 connected to the ultrasonic therapeutic device 42 to the second output terminals 42e3 and 42f3 connected to the driver 41b and 41c, respectively. This switch operation of the switch selector 41d allows the output switches 44a to be electrically connected to the drivers 41b and 41c, respectively.

Next, when the operator OP operates to turn the output switch 44a connected to the switch 41e on so as to keep the on state of the output switch 44a, the on operation input signal corresponding to the turning-on operation instruction is supplied through the switch 41e to the driver 41b.

The driver 41b causes the first electromagnetic piston 46c1 of the on-off mechanism 46 to be driven in response to the on operation input signal. This applies a pressing force with respect to the first on-off switch member 45a toward the base portion B side. This applied pressing force makes the first movable contact TC1 of the first on-off switch member 45a move toward the base portion B side.

This provides the electric connection between the first movable contact TC1 and each of the first and second fixed contacts FC1 and FC2 so that the first movable contact TC1 and each of the first and second fixed contacts FC1 and FC2 are electrically conducted to each other. This results in that the power supply unit PS and the electric scalpel device 43 are electrically conducted to each other. The electric conduction between the power supply unit PS and the electric scalpel device 43 permits electric power to be supplied from the power supply unit PS to the electric scalpel device 43, whereby he electric scalpel device 43 is turned on.

As a result, operating by the operator OP the first foot switch 44 without operating the second foot switch 45 corresponding to the electric scalpel device 43 allows the electric scalpel device 43, which does not correspond to the first foot switch 44, to be turned on. The operator uses the electric scalpel device 43 to treat the surgical field of the patient P.

On the other hand, when the treatment of the surgical field by the operator OP using the electric scalpel device 43 is completed, the operator OP operates to turn the continuously turn-on output switch 44a off. This results in that the supply of the drive signal from the driver 41b to the first movable contact TC1 is stopped so that the pressing force applied with respect to the first on-off switch member 45a is released.

This makes the first movable contact TC1 move away from the base portion B side. This movement of the first movable contact TC1 separates the electric contact between the first movable contact TC1 and each of the first and second fixed contact FC1 and FC2 so that the electric connection between the first and second fixed contacts FC1 and FC2 is broken. This causes the supply of the electric power from the power supply unit PS to the electric scalpel device 43 to be shut sown, allowing the electric scalpel device 43 to be turned off.

Incidentally, if the output switch 44a connected to the switch 41f is operated so that the on operation input signal is supplied through the switch 41f to the driver 41c, the driver 41c in place of the driver 41b can execute the same operations as the driver 41b, so that the explanations of the operations are omitted.

As described above, in the second embodiment, on and off operations of the first foot switch 44 corresponding to one of the therapeutic treatment devices (ultrasonic treatment device 42, the electric scalpel device 43) whose specifications are different from each other causes the on-off mechanism 46 to operate. The operation of the on-off mechanism 46 permits the second foot switch 45 whose specifications are different from the first foot switch 44 to be turned on and off.

This provides the medical system 40 composed of therapeutic treatment devices whose specifications are different from each other and foot switches corresponding to the therapeutic treatment devices, despite differences of the specifications of the therapeutic treatment devices and those of the specifications of the foot switches.

In addition, changing the selection of one of the screw holes 46f1, 46f2, . . . into which the fitting screw 46b is screwed allows adjustment of the positional relationship between each of the first and second pistons 46c1 and 46c2 and each of pressed surfaces 45a1 and 45b1 of the first and second on-off switches 45a and 45b.

This feature makes it possible to adjust the reciprocating ranges of the first and second on-off switch members 45a and 45b based on the operations of the first and second electromagnetic pistons 46c1 and 46c2.

As a result, even if foot switches each having the operating ranges in which the movable contacts are moved up to the connection of the fixed contacts based on the movements of the on-off switch members are different from each other, combination of the on-off mechanism 46 to the foot switches permits all of the foot switches to be turned on and off.

This makes it possible to expand the range of combinations of a plurality of therapeutic treatment devices whose specifications are different from one another, thereby designing an efficient medical system.

In the second embodiment, the first and second electromagnetic pistons 46c1 and 46c2 that cause the first and second on-off switch members 45a and 45b to operate are used, but the present invention is not limited to the structure. For example, as mechanisms cause the first and second on-off switch members 45a and 45b to reciprocate under the control of the drivers 41b and 41c, electromagnetic plungers, electromagnetic solenoids, or other similar mechanisms, which are capable of reciprocating the first and second on-off switch members 45a and 45b may be applied.

It may be possible to combine the structure related to the first embodiment with that related to the second embodiment to constitute a medical system, providing both effects of the first and second embodiments.

Next, a modification of the on-off mechanism according to the second embodiment will be explained with reference to FIG. 15.

An on-off mechanism 51 according to the modification for operating the second foot switch 45 has first and second switch operating mechanisms 51a and 51b that are designed to independently press the first and second on-off switch members 45a and 45b, respectively.

The first and second switch operating mechanisms 51a and 51b have first and second motors 52a and 52b, and first and second supporting members SM1 and SM2. The first supporting member SM1 supports the first motor 52a parallel to one side surface of the base portion B and opposite to the top surface of the base portion B. The second supporting member SM2 supports the second motor 52b parallel to the other side surface of the base portion B and opposite to the top surface of the base portion B. The first and second on-off switch members 45a and 45b are mounted on the top surface of the base portion B.

The first and second motors 52a and 52b are arranged so that their first and second rotating shafts RS1 and RS2 extend along the pressed surfaces 45a1 and 45b1 of the first and second on-off switch members 45a and 45b up to positions opposite to the pressed surfaces 45a1 and 45b1 of the first and second on-off switch members 45a and 45b, respectively.

The first and second switch operating mechanisms 51a and 51b are provided with first and second eccentric cams 53a and 53b fixed to the first and second rotating shafts RS1 and RS2, respectively.

The first and second eccentric cams 53a and 53b have substantially circular plate shapes, respectively. The first rotating shaft RS1 is fixed to one peripheral end side of one surface of the first eccentric cam 53a so that the first rotating shaft RS1 is substantially orthogonal to the one surface of the first eccentric cam 53a. The second rotating shaft RS2 is fixed to one peripheral end side of one surface, which is opposite to the one surface of the first eccentric cam 53a, of the second eccentric cam 53b so that the second rotating shaft RS2 is substantially orthogonal to the one surface of the second eccentric cam 53b.

That is, in a state that the one peripheral end of the first eccentric cam 53a is positioned in opposite to the first on-off switch member 45a, the first motor 52a causes the first eccentric cam 53a to rotate substantially 180 degrees. This rotation of the first eccentric cam 53a applies a pressing force at the other peripheral end of the first eccentric cam 53a to the first on-off switch member 45a (see FIG. 15).

Similarly, in a state that the one peripheral end of the second eccentric cam 53b is positioned in opposite to the second on-off switch member 45b, the second motor 52b makes the second eccentric cam 53b rotate substantially 180 degrees. This rotation of the second eccentric cam 53b presses at the other peripheral end of the second eccentric cam 53b the second on-off switch member 45b (see FIG. 15).

In the state that each of the one peripheral ends of the first and second eccentric cams 53a and 53b presses each of the first and second on-off switch members 45a and 45b, each of the first and second motors 52a and 52b causes each of the first and second eccentric cams 53a and 53b to rotate substantially 180 degrees. This rotation of each of the first and second eccentric cams 53a and 53b releases the pressing force applied to each of the first and second on-off switch members 45a and 45b to be kept away from each of the first and second on-off switch members 45a and 45b.

The first and second motors 52a and 52b are electrically connected to the drivers 41b and 41c, respectively.

Incidentally, other structures of the on-off mechanism 51 are substantially identical with those of the on-off mechanism 46 according to the second embodiment.

In the modification of the second embodiment, as well as the second embodiment, the on/off operation of the output switch 44a of the foot switch 44, which is connected to the driver 41b, causes the first motor 52a of the on-off mechanism 51 to rotate. This rotation of the first motor 52a makes the first eccentric cam 53a rotate, which permits the first eccentric cam 53a to press the first on-off switch member 45a or to release it from the pressed state of the first on-off switch member 45a.

Incidentally, if the operator OP operates to turn on or off of the output switch 44a of the foot switch 44, which is connected to the driver 41b, the second motor 52b of the on-off mechanism 51 rotates. The rotation of the second motor 52b makes the second eccentric cam 53b rotate, which permits the second eccentric cam 53b to press the second on-off switch member 45b or to release the pressing force applied to the second on-off switch member 45b.

As described above, even if the therapeutic treatment devices whose specifications are different from each other and foot switches whose specifications are also different from each other, the modification of the second embodiment can provide the medical system composed of these therapeutic treatment devices and the foot switches despite differences of the specifications of the therapeutic treatment devices and those of the specifications of the foot switches.

In addition, changing the geometry of each of the eccentric cams 53*a* and 53*b*, for example, the diameter of each of the eccentric cams 53*a* and 53*b*, permits adjustment of the positional relationship between each of the first and second eccentric cams 53*a* and 53*b* and each of pressed surfaces 45*a*1 and 45*b*1 of the first and second on-off switches 45*a* and 45*b*.

This feature makes it possible to adjust the reciprocating ranges of the first and second on-off switch members 45*a* and 45*b* based on the operations of the first and second eccentric cams 53*a* and 53*b*.

As a result, even if foot switches each having the operating ranges in which the movable contacts are moved up to the electrical contact position with respect to the fixed contacts based on the movements of the on-off switch members are different from each other, combination of the on-off mechanism 51 to the foot switches permits all of the foot switches to be turned on and off.

This makes it possible to expand the range of combinations of a plurality of therapeutic treatment devices whose specifications are different from one another, thereby designing an efficient medical system.

Incidentally, as a control switch that enables the operator OP to select one of therapeutic treatment devices and give an operational instruction to the selected device, the foot switch that permits the operator OP to operate with the operator's foot is applied for the medical systems of the first and second embodiments. The present invention, however, is not limited to these applications.

That is, various types of control switches that allow an operator to operate them with the operator's other portions, such as hand, elbow, can be applied for the medical systems of the first and second embodiments.

While there has been described what is at present considered to be these embodiment and modifications of the invention, it will be understood that various modifications which are not described yet may be made therein, and it is intended to cover in the appended claims all such modifications as fall within the true spirit and scope of the invention.

What is claimed is:

1. A control switch detecting apparatus for detecting a control switch operable by an operator for controlling a medical device, the apparatus comprising:
    a transmitting unit;
    a receiving unit configured to receive a position signal from the transmitting unit for representing a position of at least one of the control switch and the operator, the position signal being transmitted from at least one of the control switch and the operator by the transmitting unit; and
    a determining unit configured to determine relative position information indicative of a relative positional relationship between the control switch and the operator based on the received position signal from the transmitting unit.

2. A control switch detecting apparatus according to claim 1, wherein the relative position information includes a direction of the control switch with respect to the operator.

3. A control switch detecting apparatus according to claim 1, wherein the relative position information includes a distance between the operator and the control switch.

4. A control switch detecting apparatus according to claim 1, wherein the receiving unit is installed in the control switch.

5. A control switch detecting apparatus according to claim 1, wherein the transmitting unit is adapted to be fitted to the operator and configured to transmit the position signal for representing the position of the operator, and wherein the receiving unit is configured to receive the position signal transmitted from the transmitting unit.

6. A control switch detecting apparatus according to claim 1, further comprising an output unit configured to output the relative position information as information recognizable by the operator.

7. A control switch detecting apparatus according to claim 1, wherein the receiving unit comprises a plurality of receiving elements that operate to receive the position signal transmitted from at least one of the control switch and the operator, respectively, and the determining unit is configured to determine the relative position information between the control switch and the operator based on the position signals individually received by the receiving elements.

8. A control switch detecting apparatus according to claim 5, wherein the receiving unit comprises a plurality of receiving antennas having individually receiving directivities with respect to the position signal around the receiving unit along a surface on which the operator is movable, respectively, and the receiving antennas operating to receive the position signal transmitted from the operator in their individual receiving directivities, respectively.

9. A control switch detecting apparatus according to claim 8, wherein said determining unit is configured to compare intensities of the position signals received by the receiving antennas with one another to determine the relative position information between the operator and the control switch based on a result of the comparison.

10. A control switch detecting apparatus according to claim 5, wherein the receiving unit comprises a receiving antenna having a receiving directivity with respect to the position signal in a predetermined direction along a surface on which the operator is movable, and a rotating mechanism configured to rotate the receiving directivity of the receiving antenna around the receiving unit.

11. A control switch detecting apparatus according to claim 1, wherein the transmitting unit is installed in the control switch and configured to transmit the position signal for representing the position of the control switch, and wherein the receiving unit is configured to receive the position signal transmitted from the transmitting unit.

12. A control switch detecting apparatus according to claim 1, wherein the transmitting unit is adapted to be fitted to the operator and operating to transmit the position signal for representing the position of the operator in response to a drive signal from an exterior of the transmitting unit, and wherein the receiving unit is configured to transmit the drive signal to the transmitting unit and to receive the position signal transmitted from the transmitting unit driven by the drive signal.

13. A control switch detecting apparatus according to claim 1, wherein the receiving unit is configured to transmit a plurality of scan signals along a surface on which the operator is movable and to receive, as the position signal, at least one echo signal based on at least one of the scan signals reflected from the operator.

14. A foot switch detecting apparatus for detecting a foot switch operable by an operator for controlling a medical device, the apparatus comprising:
    a transmitting unit adapted to be fitted to one of the foot switch and the operator and configured to transmit a position signal for representing a position of one of the foot switch and the operator;

a receiving unit adapted to be fitted to the other of the foot switch and the operator and configured to receive the position signal transmitted from the transmitting unit;

a determining unit configured to determine relative position information indicative of a relative positional relationship between the control switch and the operator based on the received position signal; and an output unit configured to output the relative position information as information recognizable by the operator.

15. A control switch comprising:

a control unit for controlling a medical device and operable by an operator, a receiving and transmitting unit configured to receive a position signal transmitted from the operator for representing a position of the operator and to transmit the received position signal to the control unit, and a switch portion configured to send, to the control unit, an operating instruction for the control unit by operation of the switch portion by the operator.

16. A method of detecting a control switch operable by an operator for controlling a medical device, the method comprising:

receiving a position signal for representing a position of at least one of the control switch and the operator, the position signal being transmitted from at least one of the control switch and the operator by a transmitting unit; and determining relative position information indicative of a relative positional relationship between the control switch and the operator based on the received position signal.

* * * * *